United States Patent
Brady-Kalnay et al.

(10) Patent No.: US 9,599,603 B2
(45) Date of Patent: Mar. 21, 2017

(54) METHODS AND COMPOSITIONS FOR MODULATING ADHESION AND MIGRATION OF CADHERIN EXPRESSING CELLS

(75) Inventors: Susann Brady-Kalnay, Cleveland, OH (US); Susan Burden-Gulley, Bay Village, OH (US)

(73) Assignee: Case Western Reserve University, Cleveland, OH (US)

( * ) Notice: Subject to any disclaimer, the term of this patent is extended or adjusted under 35 U.S.C. 154(b) by 1058 days.

(21) Appl. No.: 12/504,578

(22) Filed: Jul. 16, 2009

(65) Prior Publication Data

US 2010/0093602 A1 Apr. 15, 2010

Related U.S. Application Data

(60) Provisional application No. 61/081,186, filed on Jul. 16, 2008.

(51) Int. Cl.
| | |
|---|---|
| *G01N 33/50* | (2006.01) |
| *A61K 38/03* | (2006.01) |
| *A61K 38/12* | (2006.01) |
| *A61K 38/17* | (2006.01) |

(52) U.S. Cl.
CPC ......... *G01N 33/5005* (2013.01); *A61K 38/12* (2013.01); *A61K 38/177* (2013.01); *G01N 2333/70525* (2013.01)

(58) Field of Classification Search
CPC .......... G01N 33/5005; G01N 2333/00; A61K 38/03; A61K 38/08; A61K 38/12
USPC .................................................. 514/1.1, 21.8
See application file for complete search history.

(56) References Cited

U.S. PATENT DOCUMENTS

| | | | | |
|---|---|---|---|---|
| 6,031,072 A | * | 2/2000 | Blaschuk et al. | 530/317 |
| 6,326,352 B1 | * | 12/2001 | Blaschuk et al. | 514/17.9 |
| 7,268,115 B2 | * | 9/2007 | Gour et al. | 514/19.1 |
| 7,446,120 B2 | * | 11/2008 | Gour et al. | 514/384 |
| 2009/0131306 A1 | * | 5/2009 | Gupta et al. | 514/11 |

* cited by examiner

*Primary Examiner* — David Lukton
(74) *Attorney, Agent, or Firm* — Tarolli, Sundheim, Covell & Tummino LLP

(57) ABSTRACT

A method modulating adhesion and migration of at least one cadherin expressing cell includes administering a cadherin modulating agent to the at least one cadherin expressing cell in an amount effective to modulate cell adhesion and migration. The cadherin modulating agent includes a small molecule peptidomimetic of a peptide or cyclic peptide that comprises a cadherin cell adhesion recognition sequence. The cadherin modulating agent can promote or inhibit neurite outgrowth when applied to at least one neuron disposed on a substrate coated with a cadherin molecule.

9 Claims, 25 Drawing Sheets

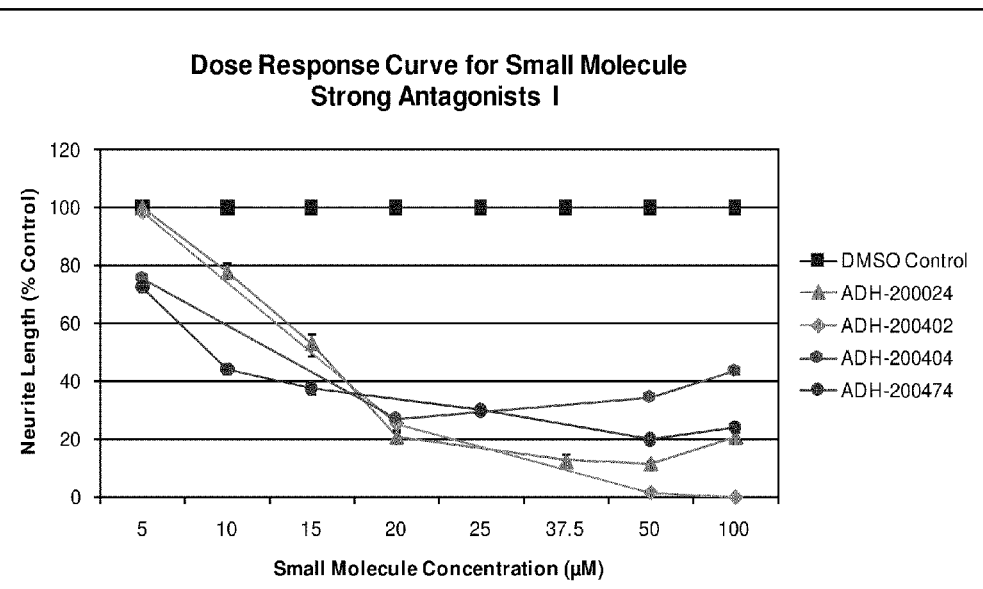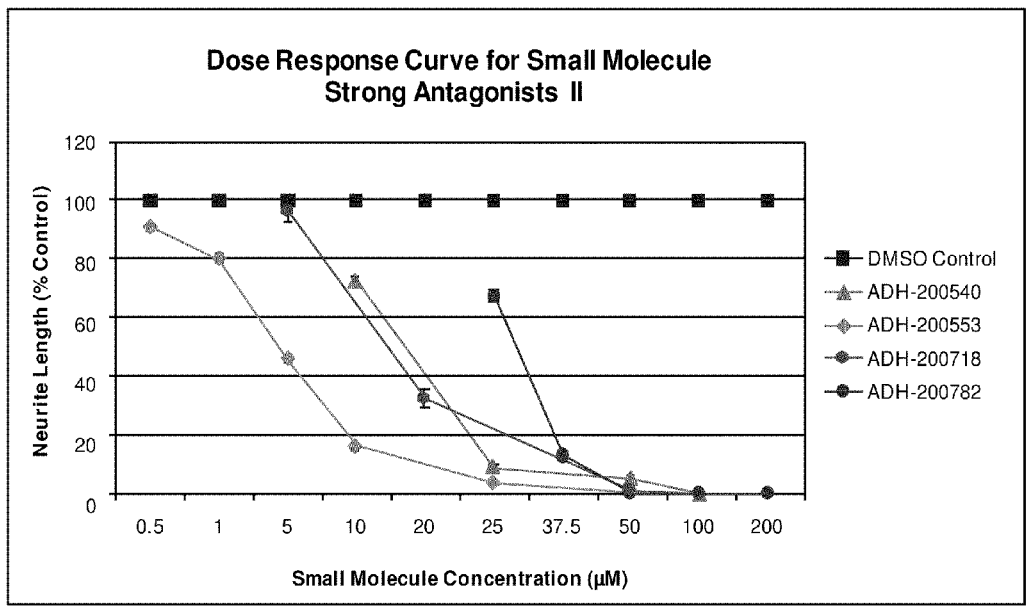
FIG. 19

SEQUENCE LISTING

<160> NUMBER OF SEQ ID NOS: 3

<210> SEQ ID NO 1
<211> LENGTH: 3
<212> TYPE: PRT
<213> ORGANISM: Homo sapiens

<400> SEQUENCE: 1

His Ala Val

```
1

<210> SEQ ID NO 2
<211> LENGTH: 3
<212> TYPE: PRT
<213> ORGANISM: Homo sapiens

<400> SEQUENCE: 2

Gln Ala Val
1

<210> SEQ ID NO 3
<211> LENGTH: 5
<212> TYPE: PRT
<213> ORGANISM: Homo sapiens

<400> SEQUENCE: 3

Cys His Ala Val Cys
1               5
```

METHODS AND COMPOSITIONS FOR MODULATING ADHESION AND MIGRATION OF CADHERIN EXPRESSING CELLS

RELATED APPLICATION

This application claims priority from U.S. Provisional Application No. 61/081,186, filed Jul. 16, 2008, the subject matter, which is incorporated herein by reference in its entirety.

TECHNICAL FIELD

The present invention relates generally to methods and compositions for modulating (e.g., enhancing or inhibiting) adhesion and migration of cadherin expressing cell, and to methods of identifying cadherin modulating agents that enhance (agonists) or inhibit (antagonists) cadherin-dependent cell adhesion and migration.

BACKGROUND OF THE INVENTION

Cadherins comprise a large family of cell adhesion molecules (CAMs) that mediate cell-cell adhesion. The type I classical cadherins, which include epithelial (E)-cadherin and neuronal (N)-cadherin, are homophilic, calcium-dependent CAMs. Although originally identified based on the cell type in which they were discovered, both E- and N-cadherin are found throughout the body. N-cadherin stabilizes cell-cell adhesions at neuronal synapses but also promotes cell migration during tissue morphogenesis and neuronal growth cone guidance. Structurally, type I cadherins have five extracellular cadherin (EC) domain repeats, a transmembrane segment and a highly conserved cytoplasmic segment. The site of homophilic binding lies in the distal-most EC domain, EC1. Both the His-Ala-Val (HAV) sequence (SEQ ID NO: 1) and the Trp2 residue are unique to classical cadherins and regulate homophilic binding. In fact, both peptides and cyclic peptides that comprise the HAV sequence of N-cadherin are sufficient to disrupt cell-cell adhesion and neurite outgrowth. Atypical (type II) cadherins, such as Cadherin-11, also have cell adhesion recognition sequences that have been identified and can be targeted in a similar fashion.

SUMMARY OF THE INVENTION

The present invention relates to methods and compositions for enhancing or inhibiting adhesion and migration of cadherin expressing cells, and to methods of identifying cadherin modulating agents that enhance or inhibit cadherin-dependent cell adhesion and migration.

One aspect of the present invention relates to a method for modulating adhesion and migration of at least one cadherin expressing cell. The method includes administering a cadherin modulating agent to the at least one cadherin expressing cell in an amount effective to modulate cell adhesion. The cadherin modulating agent includes a small molecule peptidomimetic that is similar (e.g., has a similar or substantially similar three dimensional structure) to a cyclic peptide (e.g., ADH-1), which comprises a cadherin cell adhesion recognition sequence (e.g., HAV (SEQ ID NO: 1). The cadherin modulating agent can promote or inhibit neurite outgrowth when applied to at least one neuron disposed on a substrate coated with a cadherin molecule.

Another aspect of the present invention relates to a method for modulating neurite outgrowth and neuronal migration. One step of the method can include administering a cadherin modulating agent to at least one neuron in an amount effective to modulate neurite outgrowth. The cadherin modulating agent includes a small molecule peptidomimetic that is similar to a peptide or cyclic peptide, which comprises a cadherin cell adhesion recognition sequence. The cadherin modulating agent can promote or inhibit neurite outgrowth when applied to at least one neuron disposed on a substrate coated with a cadherin molecule.

Another aspect of the present invention relates to method of treating an injury of the nervous system in a subject. One step of the method can include administering a therapeutically effective amount of a cadherin agonist to the subject. The cadherin agonist includes a small molecule peptidomimetic that is similar to a peptide or cyclic peptide, which comprises a cadherin cell adhesion recognition sequence. The cadherin agonist can promote neurite outgrowth when applied to at least one neuron disposed on a substrate coated with a cadherin molecule as compared to a control.

Another aspect of the present invention relates to a method for enhancing neuronal regeneration in a subject. One step of the method can include administering a therapeutically effective amount of a cadherin agonist to the subject. The cadherin agonist includes a small molecule peptidomimetic that is similar to a peptide or cyclic peptide, which comprises a cadherin cell adhesion recognition sequence. The cadherin agonist can promote neurite outgrowth when applied to at least one neuron disposed on a substrate coated with a cadherin molecule as compared to a control.

A further aspect of the present invention relates to a method for treating aberrant neuronal migration disorders in a subject. One step of the method can include administering a therapeutically effective amount of a cadherin antagonist to the subject. The cadherin antagonist includes a small molecule peptidomimetic that is similar to a peptide or cyclic peptide, which comprises a cadherin cell adhesion recognition sequence. The cadherin antagonist can inhibit neurite outgrowth when applied to at least one neuron disposed on a substrate coated with a cadherin molecule as compared to a control.

Another aspect of the present invention relates to a method for identifying a cadherin modulating agent capable of modulating neurite outgrowth. One step of the method can include applying a potential cadherin modulating agent to at least one neuron disposed on a substrate coated with a cadherin molecule. The potential cadherin modulating agent includes a small molecule peptidomimetic that is similar to a peptide or cyclic peptide, which comprises a cadherin cell adhesion recognition sequence. Next, neurite outgrowth on the substrate can be evaluated. An increase or decrease in neurite outgrowth of the at least one neuron as compared to a control indicates that the potential cadherin modulating agent is a cadherin modulating agent capable of modulating neurite outgrowth.

Another aspect of the present invention relates to a method for treating cancer in a subject. The method includes administering a therapeutically effective amount of a cadherin antagonist. The cadherin antagonist can include a small molecule peptidomimetic that is similar to a peptide or cyclic peptide, which comprises a cadherin cell adhesion recognition sequence. The cadherin antagonist can inhibit neurite outgrowth when applied to at least one neuron disposed on a substrate coated with a cadherin molecule.

Another aspect of the present invention relates to a method for treating cancer in a subject. One step of the method can include administering a therapeutically effective amount of a cadherin agonist alone or in combination with a cadherin antagonist to the subject. The cadherin agonist and/or the cadherin antagonist can include small molecule peptidomimetics that are similar to a peptide or cyclic peptide, which comprises a cadherin cell adhesion recognition sequence. In one example, the cadherin agonist can promote neurite outgrowth when applied to at least one neuron disposed on a substrate coated with an E-cadherin molecule. In another example, the cadherin antagonist can promote neurite outgrowth when applied to at least one neuron disposed on a substrate coated with an N-cadherin molecule.

BRIEF DESCRIPTION OF THE DRAWINGS

The foregoing and other features of the present invention will become apparent to those skilled in the art to which the present invention relates upon reading the following description with reference to the accompanying drawings.

FIG. 19 illustrates dose response curves of the strong small molecule antagonists reduction of neurite length on N-cadherin. Error bars represent standard error.

DETAILED DESCRIPTION

Figure 1:
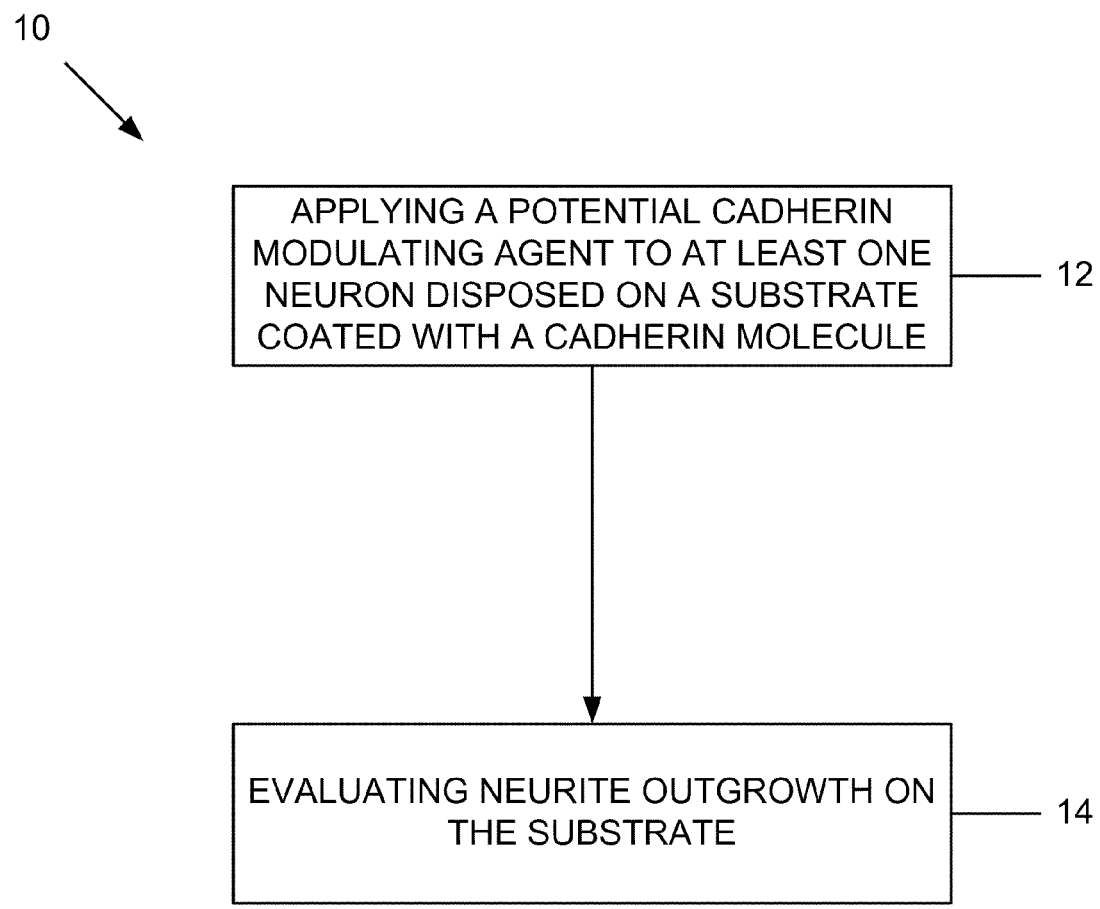
FIG. 1 is a flow diagram illustrating a method for identifying a cadherin modulating agent in accordance with one aspect of the present invention.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

In the context of the present invention, the term "peptide" or "polypeptide" refers to an oligopeptide, peptide, or protein sequence, or to a fragment, portion, or subunit of any of these, and to naturally occurring or synthetic molecules. The term "polypeptide" also includes amino acids joined to each other by peptide bonds or modified peptide bonds, i.e., peptide isomers, and may contain any type of modified amino acids. The term "polypeptide" also includes peptides and polypeptide fragments, motifs and the like, glycosylated polypeptides, all "mimetic" and "peptidomimetic" polypeptide forms, and retro-inversion peptides (also referred to as all-D-retro or retro-enantio peptides). The term can also include linear and cyclic polypeptides.

As used herein, the term "polynucleotide" refers to oligonucleotides, nucleotides, or to a fragment of any of these, to DNA or RNA (e.g., mRNA, rRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, siRNAs, microRNAs, and ribonucleoproteins. The term also encompasses nucleic acids, i.e., oligonucleotides, containing known analogues of natural nucleotides, as well as nucleic acid-like structures with synthetic backbones.

As used herein, the term "subject" refers to any warm-blooded organism including, but not limited to, human beings, pigs, rats, mice, dogs, goats, sheep, horses, monkeys, apes, rabbits, chickens, cattle, etc.

As used herein, the term "effective amount" refers to a dosage of a cadherin modulating agent that is sufficient to provide treatment for a disease, such as an injury of the nervous system or cancer. The effective amount can vary depending on the subject, the injury being treated, and the treatment being affected.

As used herein, the term "cadherin modulating agent" refers to a small molecule peptidomimetic that is similar to a peptide or cyclic peptide including a cadherin cell adhesion recognition sequence and is capable of promoting or inhibiting neurite outgrowth when applied to at least one neuron disposed on a substrate coated with a cadherin molecule.

As used herein, the term "cadherin agonist" refers to a cadherin modulating agent that, when applied to at least one neuron disposed on a substrate coated with a cadherin molecule, results in increased neurite outgrowth.

As used herein, the term "cadherin antagonist" refers to a cadherin modulating agent that, when applied to at least one neuron disposed on a substrate coated with a cadherin molecule, results in decreased neurite outgrowth.

As used herein, the term "therapeutically effective amount" refers to that amount of a cadherin modulating agent that relieves to some extent one or more symptoms of a disease, such as a nervous system injury (e.g., an neurodegenerative disease or trauma to the nervous system) or returns to normal, either partially or completely, one or more physiological or biochemical parameters associated with or causative of the disease, results in increased neurite outgrowth, results in decreased neurite outgrowth, decreased cadherin-dependent adhesion, decreased cancer growth, amelioration of symptoms, and/or a prolongation of survival in a subject (e.g., agonist or antagonist).

As used herein, the term "cell adhesion molecule" refers to a molecule capable of mediating the joining of two or more cells (cell adhesion) or adhesion between a substrate and a cell. In general, cell adhesion molecules are divided into two groups: molecules involved in cell-cell adhesion (intercellular adhesion) (cell-cell adhesion molecules) and molecules involved in cell-extracellular matrix adhesion (cell-substrate adhesion) (cell-substrate adhesion molecules). Examples of cell adhesion molecules are provided below.

As used herein, the term "nervous system" includes both the peripheral nervous system (PNS) and the central nervous system (CNS).

As used herein, the term "cyclic peptide" refers to a peptide or derivative thereof that comprises: (1) an intramolecular covalent bond between two non-adjacent residues; and (2) at least one cadherin cell adhesion recognition sequence including, but not limited to, HAV (His-Ala-Val) (SEQ ID NO: 1) and QAV (Gln-Ala-Val)(SEQ ID NO: 2). The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization).

As used herein, the term "neurite" refers to any process growing out of a neuron. The term also encompasses all such cell processes (including both axon and dendrite) growing out of a neuron.

As used herein, the term "neurite outgrowth" refers to the process of cells growing out of a neuron, or to the neurons growing out of an explant.

As used herein, the term "neuronal migration" refers to the ability of neuronal cells to migrate or neuronal processes to migrate such as an axonal or dendritic migration.

The present invention relates generally to methods and compositions for enhancing or inhibiting adhesion and migration of cadherin expressing (e.g., neurite outgrowth and neuronal migration, cancer cell growth), and to methods of identifying cadherin modulating agents that enhance (i.e., agonists) or inhibit (i.e., antagonists) cadherin-dependent cell adhesion and migration. The present invention also provides a method for modulating adhesion and migration of at least one cadherin expressing cell, a method for modulating neurite outgrowth and neuronal migration, a method for treating an injury of the nervous system in a subject, a method for enhancing neuronal regeneration in a subject, a method for identifying a cadherin modulating agent capable of modulating neurite outgrowth, and a method of treating cancer in a subject.

It was found that neurite outgrowth assays in which at least one neuron is disposed on a substrate coated with a cell adhesion molecule, such as a cadherin molecule, can be used to identify cadherin modulating agents that enhance or inhibit cadherin-dependent neurite outgrowth as well as inhibit cancer growth and progression. It was further found that a neurite outgrowth assay in accordance with the present invention provides a relatively simple test that mimics a very complex cellular process, which includes cell adhesion, cell migration and cell survival, and is an excellent in vitro system to identify cadherin modulating agents that are efficacious in inhibiting complex cellular processes in vivo.

In one example, potential cadherin modulating agents can be applied to at least one neuron (e.g., retinal ganglion cell (RGC)) disposed on a substrate coated with a cadherin molecule (e.g., E-cadherin, N-cadherin, P-cadherin, R-cadherin, and cadherin-11 (OB-cadherin) etc.). The potential cadherin modulating agent can include a small molecule peptidomimetic or "non-peptidyl analogue" that has a similar or substantially similar three-dimensional structure of a cadherin cell adhesion recognition sequence including, but not limited to, HAV (His-Ala-Val) (SEQ ID NO: 1) and QAV (Gln-Ala-Val)(SEQ ID NO: 2). Methods of identifying potential small molecule peptidomimetics of cadherin cell adhesion recognition sequences are disclosed in U.S. Pat. Nos. 7,268,115 and 7,446,120, both of which are incorporated by reference in their entirety. Examples of potential small molecule peptidomimetics that can be screened using the assay of the present invention for agonist and antagonist activity are also disclosed in U.S. Pat. Nos. 7,268,115 and 7,446,120. For instance, U.S. Pat. No. 7,446,120 discloses a number of small molecule peptidomimetics that potentially mimic the three-dimensional structure of the ADH-1 short cyclic peptide, comprised of the HAV (SEQ ID NO: 1) cadherin cell adhesion recognition sequence. The small molecules are shown in FIGS. 15A-15BG (compounds 13-282) and FIGS. 17A-17j (compounds 283-311), FIGS. 18A-18E (compounds 312-331), FIGS. 19A-19E (compounds 332-334), FIGS. 21A-21N (compounds 345-399), FIGS. 29A-29G (compounds 465-481), and FIGS. 31A-31AI (compounds 482-593) of U.S. Pat. No. 7,446,120.

In one example, small molecule peptidomimetics with three-dimensional similarities to ADH-1 can be assayed by administering the small molecule peptidomimetics to retinal ganglion cell (RGC) provided on an N-cadherin substrate and then comparing the RGC neurite outgrowth to vehicle control treated cultures to determine their potential agonist or antagonist activity. It will appreciated that any one, combination, derivative, or functional equivalent of the small molecules peptidomimetics disclosed in U.S. Pat. Nos. 7,268,115 and 7,446,120 as well as other small molecules peptidomimetics that are substantially similar to cadherin cell recognition sequence can be potentially screened using the neurite outgrowth assay of the present invention for antagonist or agonist activity.

Cadherin modulating agents that act as an agonist and that are identified in vitro by the neurite outgrowth assay of the present invention can be used in vivo to treat a subject with an injury to the central nervous system. In one example, the cadherin modulating agents can include cadherin agonists that are administered to a subject with a neural injury to promote neuronal regeneration.

Cadherin modulating agents that act as antagonists identified in vitro by the neurite outgrowth assay of the present invention can be used in vivo to treat neuronal disorders, such as neuronal disorders that result from aberrant axonal outgrowth (e.g., neuropathic pain or allodynia). In one example, neuropathic pain can result from aberrant sprouting of primary sensory neuronal processes within the injured dorsal horn of the spinal cord, leading to incorrect innervation of non-target neurons or tissues. N-cadherin is expressed in the dorsal horn of adult spinal cord and its expression is maintained after sciatic nerve injury, another experimental model of neuropathic pain. Because of its ability to promote neurite outgrowth, N-cadherin is likely to contribute to aberrant neuronal sprouting within the spinal cord following injury. Antagonists in accordance with the present invention can reduce the level of aberrant sprouting and subsequent neuropathic pain experienced following spinal cord injury.

Cadherin modulating agents that act as antagonists identified in vitro by the neurite outgrowth assay of the present invention can also be used in vivo to treat cancer metastases. A switch in expression of E- to N-cadherin has been observed in a number of carcinomas, including melanoma, prostate and breast cancer. N-cadherin has also been implicated in mediating tumorigenesis in gliomas and in tumors that migrate or invade nervous tissue, including pancreatic cancer. It is hypothesized that expression of N-cadherin in breast cancer cells is responsible for promoting metastasis, by promoting cancer cell migration. Antagonists identified in accordance with the present invention can be effective cancer therapies by inhibiting N-cadherin-mediated adhesion and migration of cancer cells. Furthermore, in one example, agonists of E-cadherin may also be of therapeutic value in treating cancer.

FIGS. 1-4 are flow diagrams illustrating a method 10 for identifying a cadherin modulating agent capable of modulating neurite outgrowth. The method 10, at step 12, can include applying a potential cadherin modulating agent to at least one neuron disposed on a substrate coated with a cell adhesion molecule. For example, the potential cadherin modulating agent can be applied to at least one retinal ganglion cell (RGC) disposed on a substrate coated with a cadherin molecule. In another example, the neuron may be a dorsal root ganglion neuron or a hippocampal neuron. The potential cadherin modulating agent can include a small molecule peptidomimetic that is similar to a peptide or cyclic peptide, which comprises a cadherin cell adhesion recognition sequence, or any one, combination, derivative, or functional equivalent of the small molecule peptidomimetics disclosed in U.S. Pat. Nos. 7,268,115 and 7,446,120.

Figure 2:
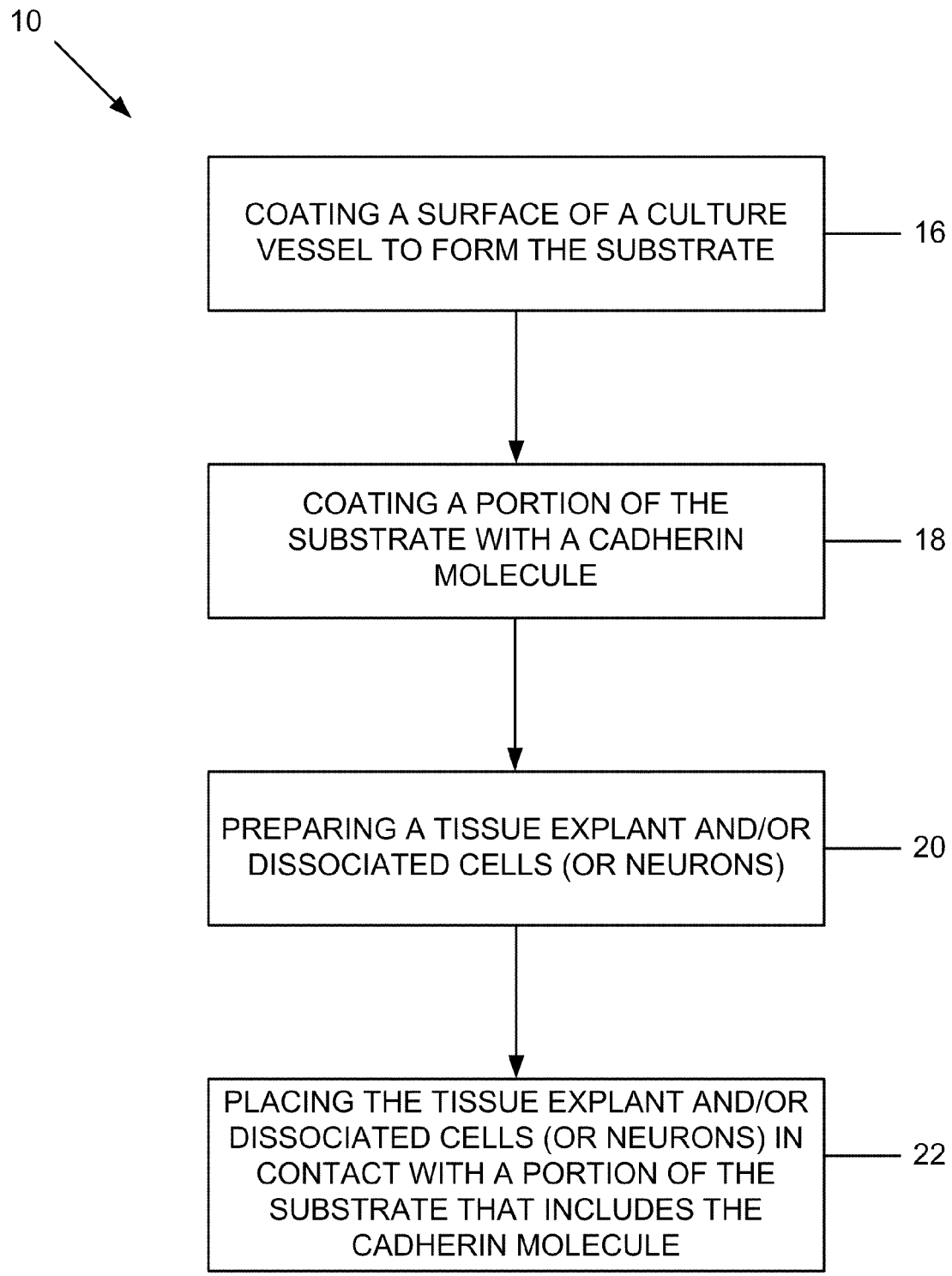
FIG. 2 is a flow diagram illustrating a further aspect of the method in FIG. 1.

Prior to applying the potential cadherin modulating agent to the at least one neuron, the method 10can include coating a surface of a culture vessel to form the substrate at 16 (FIG. 2). For example, the surface of the culture vessel can be directly or indirectly coated with nitrocellulose. The culture vessel can include any known vessel, chamber, or other device suitable for in vitro cell culture or cell analysis. Examples of culture vessels can include, but are not limited to, tissue culture dishes (e.g., 35 mm or 60 mm Petri or tissue culture-coated dishes), 6-well plates, 12-well plates, 24-well plates, and 96-well plates. The nitrocellulose can be entirely or partly dissolved in a solvent, such as methanol to facilitate coating onto the surface of the culture vessel. It will be appreciated that other known materials besides nitrocellulose which are capable of providing polypeptide binding sites may also be used to coat the surface of the culture vessel.

After coating the surface of the culture vessel, a portion of the substrate can be coated with at least one cell adhesion molecule at 18. The at least one cell adhesion molecule can be selected from one of the known cell adhesion molecule cadherin superfamily of cell adhesion molecules. For example, the at least one cell adhesion molecule can comprise a cadherin molecule. Cadherin molecules can include any of the type-1 transmembrane proteins that play a role in cell adhesion and include both classical and non-classical cadherins, which are generally dependent on calcium to function. Examples of cadherin molecules can include E-cadherin, N-cadherin, P-cadherin, R-cadherin, and cadherin-11 (OB-cadherin). The cell adhesion molecule can include an entire cell adhesion molecule or a fragment thereof. Additionally or optionally, the cell adhesion molecule can include other biological moieties, such as functional polypeptide domains, and peptides. It should be appreciated that the cell adhesion molecule may also be directly coated onto the surface of the culture vessel without first coating the surface with nitrocellulose, for example.

In an example of the method 10, a cell adhesion molecule, such as E-cadherin can be coated onto a portion of the substrate. The substrate can include a nitrocellulose-coated, 35 mm tissue culture dish. Submicrogram quantities of E-cadherin can be spread across the center of the tissue culture dish and then incubated for about 20 minutes at about room temperature. Any remaining binding sites on the nitrocellulose can be blocked using about 2% BSA. The tissue culture dishes can then be rinsed with an appropriate medium.

Figure 3:
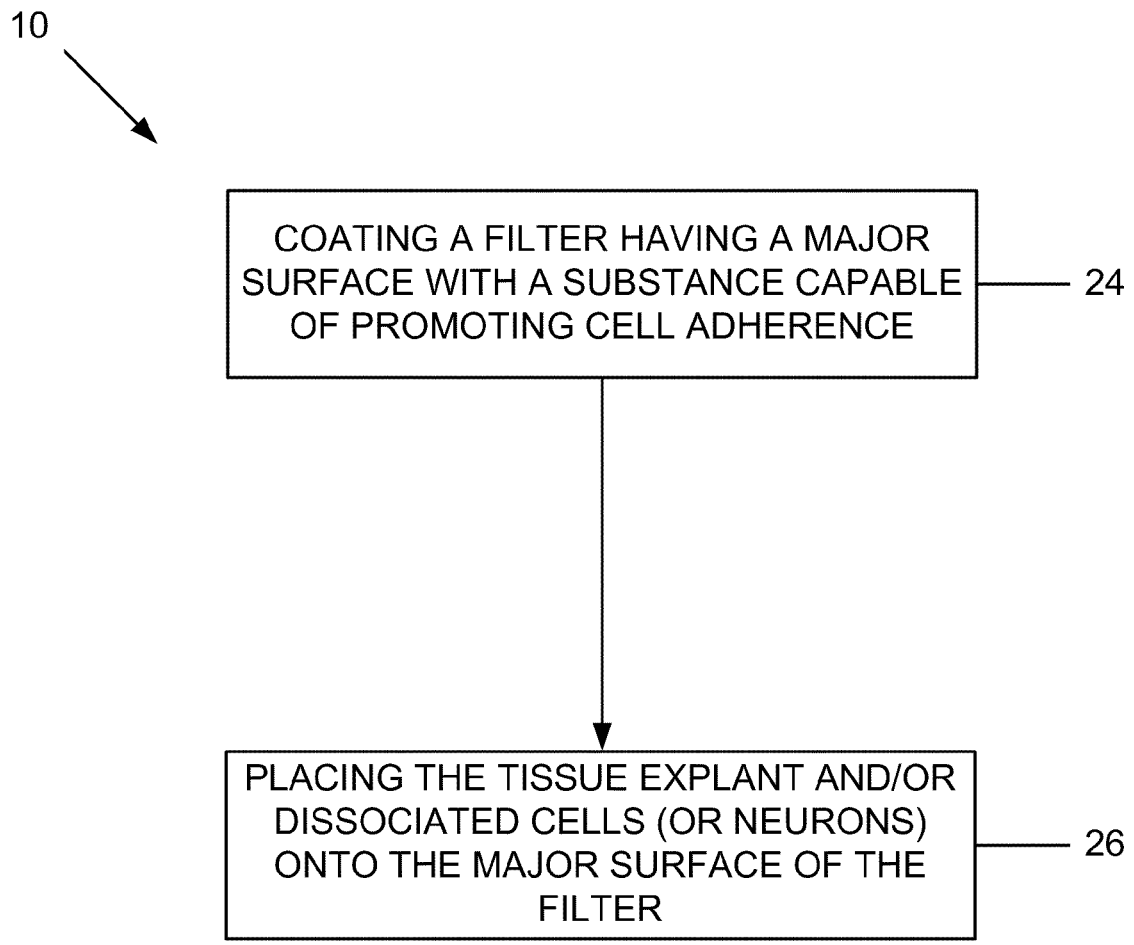
FIG. 3 is a flow diagram illustrating a further aspect of the method in FIG. 2.

At 20, a tissue explant and/or dissociated cells (or neurons) can be prepared after coating a major surface of the substrate with at least one cell adhesion molecule. As shown in FIG. 3, the tissue explant can be prepared at 24 by coating the major surface of the nitrocellulose filter with a substance capable of promoting cell adherence, such as a lectin (e.g., concavalin A). The tissue explant can include a neural retina from an embryonic day 8 White Leghorn chick eye containing RGC neurons, for example. Other examples of tissue explants can include dorsal root ganglia, including dorsal root ganglion neurons, spinal cords containing spinal motor neurons, cerebellar explants containing cerebellar neurons, cortical explants containing cortical neurons, hippocampus explants containing hippocampal neurons, and so on. At 26, the tissue explant can be placed on the concavalin A-coated nitrocellulose filter. If necessary, the tissue explant can then be cut into a desired size, such as a 350 μm wide explant.

Next, the tissue explant and/or dissociated cells can be placed in contact with the major surface of the nitrocellulose-coated culture vessel at 22 (FIG. 2). For example, the tissue explant and/or dissociated cells (or neurons) can be placed so that at least one neuron contacts the major surface of the substrate. An appropriate culture media can then be added to the culture vessel to culture the tissue explants and/or dissociated cells (or neurons). For example, a retinal neuron culture media comprising RPMI-1640, about 10% fetal bovine serum, about 2% chick serum, about 100 U/ml penicillin, about 0.1 mg/ml streptomycin, and about 0.025 μg/ml amphotericin can be used to culture the tissue explants and/or dissociated cell (or neurons). After preparing the tissue explants and/or dissociated cells (or neurons), the nitrocellulose filter can be cut into strips (if necessary). The tissue explant and/or dissociated cells (or neurons) can then be placed onto the culture vessel so that the neurons are placed directly adjacent the substratum.

Figure 4:
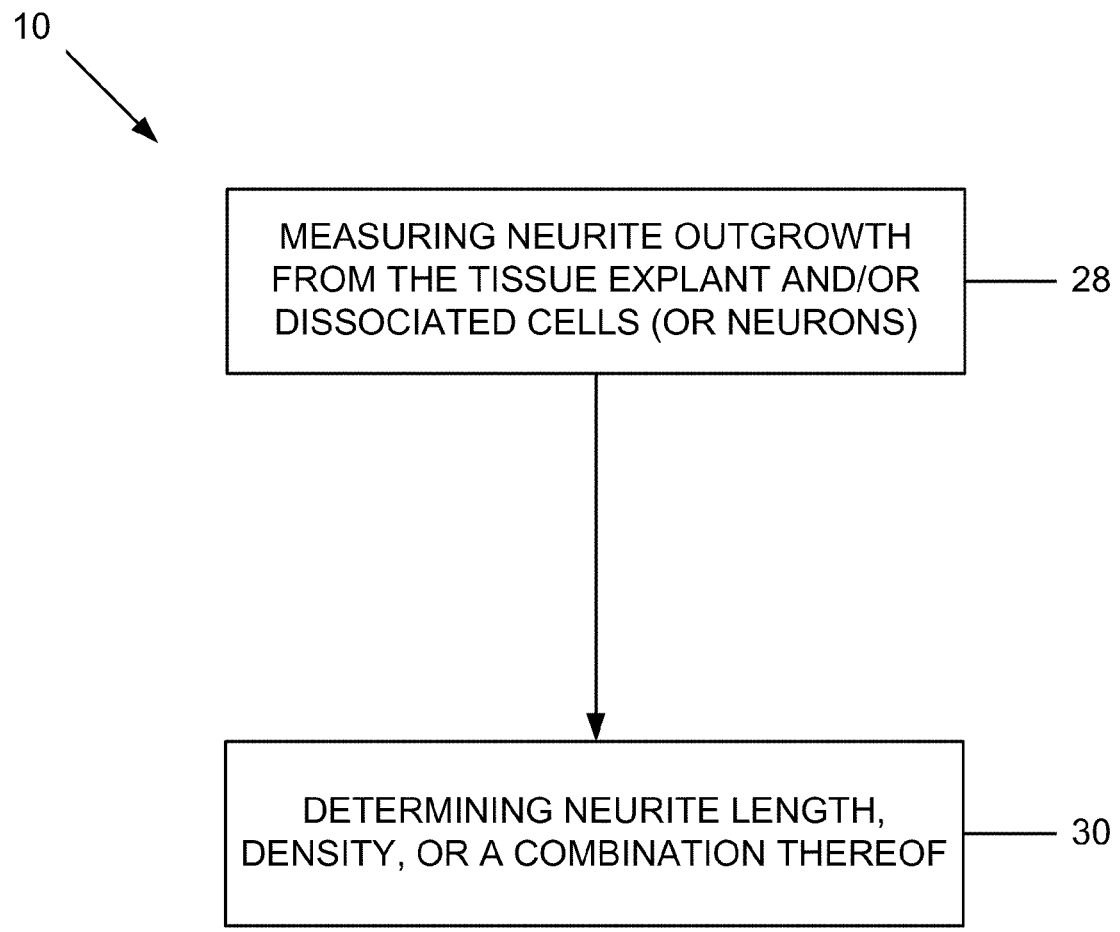
FIG. 4 is a flow diagram illustrating a further aspect of the method in FIG. 1.

After placing the tissue explant and/or dissociated cells (or neurons) into the culture vessel, the potential cadherin modulating agent can be added to the culture vessel. The potential cadherin modulating agent can be added alone or in combination with culture media. After addition of the potential cadherin modulating agent, the outgrowth of neurites can be evaluated at 14 (FIG. 1). Outgrowth of neurites can be evaluated at a desired time point, such as about 20 hours after the addition of the potential cadherin modulating agent. As shown in FIG. 4, neurite outgrowth can be evaluated by measuring neurite outgrowth from the tissue explant at 28. For example, a SPOT RT digital camera and image acquisition software can be used to capture images and measure the length, density, or a combination thereof of the longest neurite(s) per given area of the tissue explant. Additionally, neurite length and density can be determined at 30 by analyzing the digital images using Metamorph software version 6.3r4 (Universal Imaging, Downington, Pa.), for example.

After evaluating neurite outgrowth at 14, a determination can be made as to whether the potential cadherin modulating agent is a cadherin agonist or a cadherin antagonist. The determination of whether the potential cadherin modulating agent is a cadherin agonist or a cadherin antagonist can be made by evaluating neurite outgrowth as compared to a control. For example, where increased neurite outgrowth as compared to a control is observed, the identified cadherin modulating agent may promote or enhance neurite outgrowth (i.e., a cadherin agonist). More particularly, the potential cadherin modulating agent may be a cadherin agonist where neurite outgrowth (as compared to a control) is increased by at least about 101%, by at least about 110%, by at least about 120%, by at least about 130%, or by even more. For example, the potential cadherin modulating agent may be a cadherin agonist where neurite outgrowth (as compared to a control) is increased by at least about 120% as compared to a control. Alternatively, where decreased neurite outgrowth is observed as compared to a control, the identified cadherin modulating agent may reduce or inhibit neurite outgrowth (i.e., a cadherin antagonist). More particularly, the potential cadherin modulating agent may be a cadherin antagonist where neurite outgrowth (as compared to a control) is reduced by at least about 40%, by at least about 50%, by at least about 60%, by at least about 70%, or by even more. For example, the potential cadherin modulating agent may be a cadherin antagonist where neurite outgrowth (as compared to a control) is decreased by at least about 50% as compared to a control.

Figure 5:
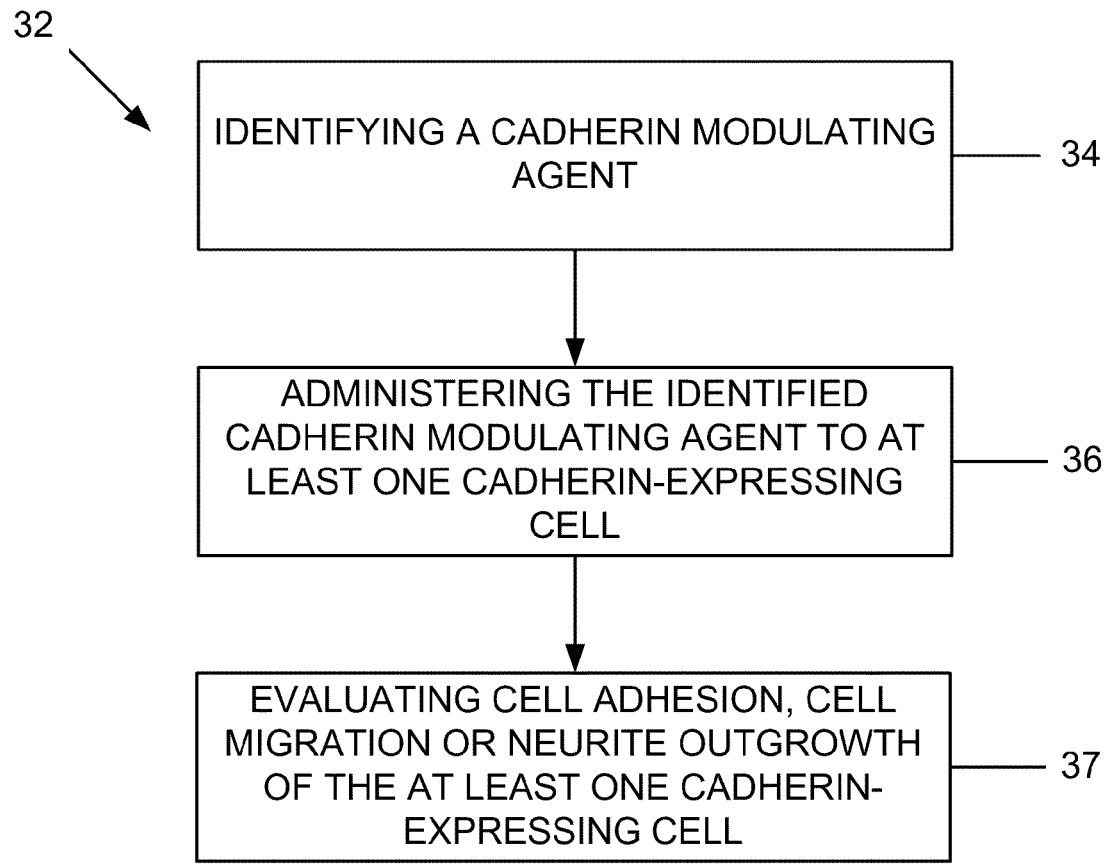
FIG. 5 is a flow diagram illustrating a method for modulating adhesion and migration of at least one cadherin expressing cell in accordance with another aspect of the present invention.

Another aspect of the present invention is illustrated in FIG. 5. In FIG. 5, a method 32 is provided for modulating adhesion and migration of at least one cadherin expressing cell. At 34, one step of the method 32 can include identifying a cadherin modulating agent. To identify a cadherin modulating agent, a neurite outgrowth assay can be performed in an identical or similar fashion as illustrated in FIGS. 1-4 and as described above. For example, a neurite outgrowth assay can be performed as described above to determine whether a potential cadherin modulating agent is a cadherin agonist or a cadherin antagonist. In another example, a retinal cell migration assay could be performed similar to FIG. 25. In a further example, a cell adhesion assay could be used similar to FIG. 20.

After identifying the cadherin modulating agent, the cadherin modulating agent can be administered to at least one cadherin expressing cell at 36 to modulate adhesion and migration of the cadherin expressing cell. A "cadherin expressing cell" may be any type of cell that expresses at least one cadherin molecule on the cell surface at a detectable level. Any one or combination of standard techniques, such as immunocytochemical protocols may be used to detect the presence or absence of cadherin molecules on the cell surface (see, e.g., Blaschuk and Farookhi, *Dev. Biol.* 136:564-567, 1989). Examples of cadherin expressing cells can include, but are not limited to, endothelial cells, epithelial cells, neuronal cells, and cancer cells.

Depending upon the type and location of the cadherin expressing cell, as well as the type of cadherin modulating agent (i.e., a cadherin agonist or antagonist) an appropriate amount of the cadherin modulating agent can administered to the cadherin expressing cell. For example, the cadherin expressing cell can be part of an in vitro system, such as part of a cultured cell line or, alternatively, part of an ex vivo system, such as part of a tissue or organ system. After administering the cadherin modulating agent to the cadherin expressing cell, any one or combination of known methods can be used to evaluate the effect(s) of the cadherin modulating agent. For example, the in vivo effect(s) of a cadherin agonist can be indirectly monitored by observing the progress of symptoms associated with a disease, such as a nervous system injury (e.g., regaining lost function). Alternatively, the in vitro effect(s) of a cadherin antagonist can be monitored by directly observing neurite outgrowth, cell adhesion or cell migration using one or a combination of imaging techniques.

Figure 6:
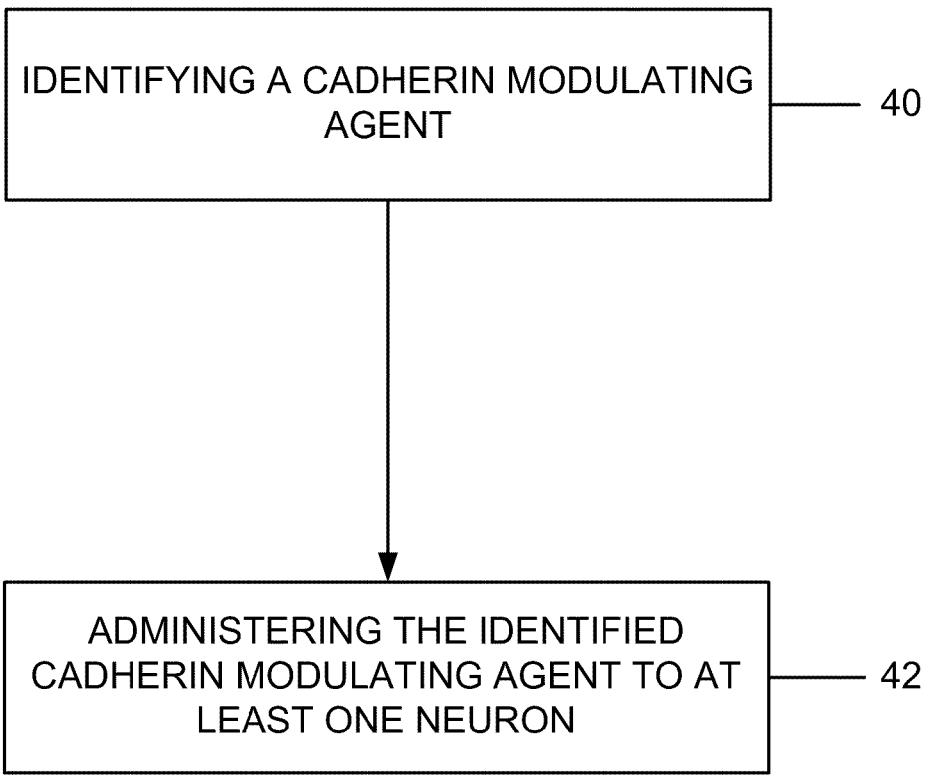
FIG. 6 is a flow diagram illustrating a method for modulating neurite outgrowth and neuronal migration in accordance with another aspect of the present invention.

Another aspect of the present invention is illustrated in FIG. 6. In FIG. 6, a method 38 is provided for modulating neurite outgrowth and neuronal migration. At 40, one step of the method 38 can include identifying a cadherin modulating agent. To identify a cadherin modulating agent, a neurite outgrowth assay can be performed in an identical or similar fashion as illustrated in FIGS. 1-4 and as described above. For example, a neurite outgrowth assay can be performed as described above to determine whether a potential cadherin modulating agent is a cadherin agonist or a cadherin antagonist.

After identifying a cadherin modulating agent that promotes or inhibits neurite outgrowth, the identified cadherin modulating agent can be administered to a neuron at 42. As used herein, a "neuron" can include any electrically excitable cell in the nervous system that processes and transmits information. For example, a neuron can include any grayish or reddish granular cell with a specialized process or processes that is the fundamental functional unit of nervous tissue. Examples of neurons to which the identified cadherin modulating agent can be administered include the neurons comprising the CNS and the PNS.

Depending upon the type of the identified cadherin modulating agent (i.e., a cadherin agonist or antagonist), the cadherin modulating agent can be administered to a neuron in an amount effective to modulate neuronal adhesion and migration. The cadherin modulating agent can be administered to the a neuron comprising part of an in vitro system, such as part of a cultured cell line or, alternatively, part of an in vivo system, such as part of a tissue or organ system (e.g., the retina, spinal cord or brain). For example, a cadherin agonist can be administered to a neuron in the spinal cord to promote neurite extension and, as described in more detail below, to promote neuronal regeneration.

Figure 7:
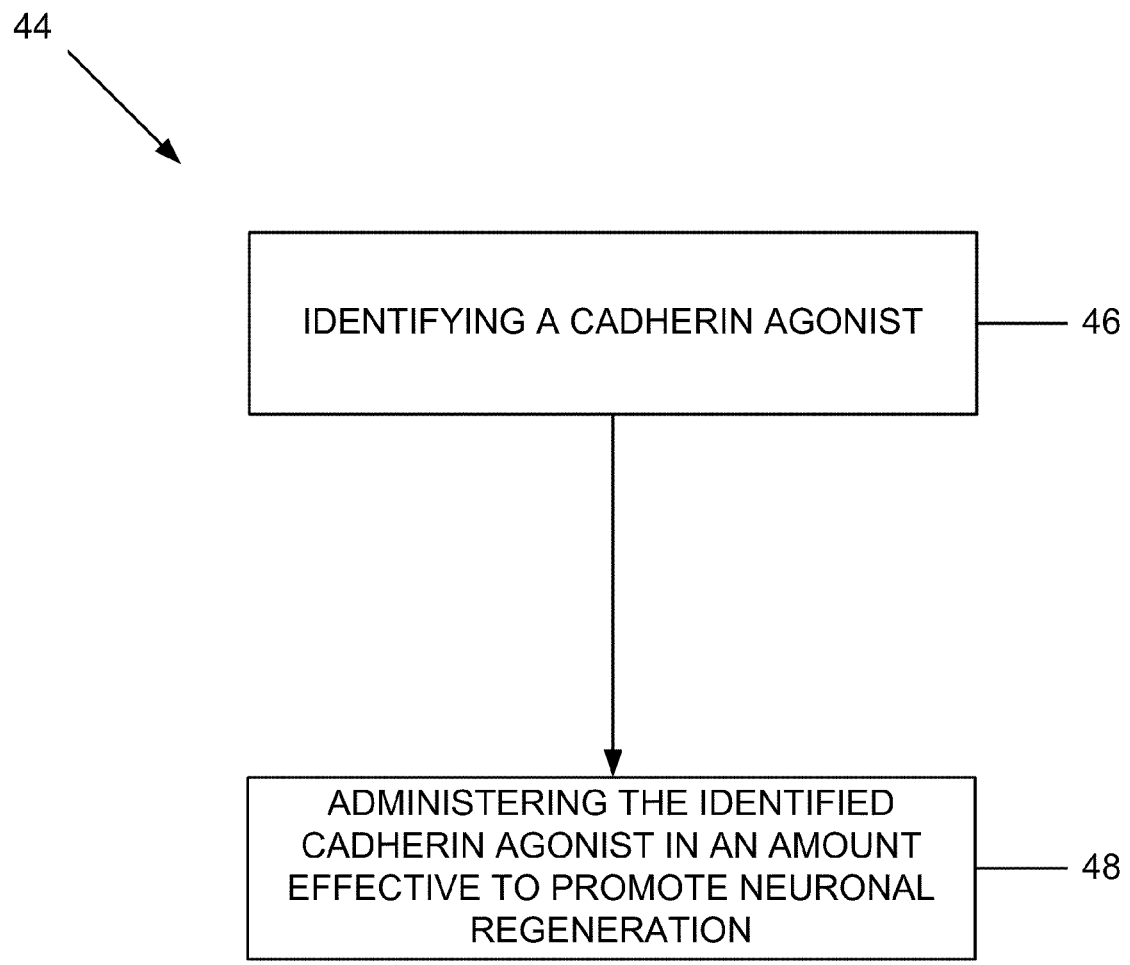
FIG. 7 is a flow diagram illustrating a method for promoting neuronal regeneration in accordance with another aspect of the present invention.

Another aspect of the present invention is illustrated in FIG. 7. In FIG. 7, a method 44 is provided for enhancing neuronal regeneration in a subject. At 46, one step of the method 44 can include identifying a cadherin agonist. To identify a cadherin agonist, a neurite outgrowth assay can be performed in an identical or similar fashion as illustrated in FIGS. 1-4 and as described above. For example, a neurite outgrowth assay can be performed to determine whether a potential cadherin modulating agent is a cadherin agonist by evaluating neurite outgrowth of at least one neuron disposed on a substrate coated with a cadherin molecule upon application of the cadherin modulating agent to the neuron. Where increased neurite outgrowth as compared to a control is observed, the identified cadherin modulating agent may promote or enhance neurite outgrowth and, thus, be a cadherin agonist.

After identifying a cadherin agonist, the identified cadherin agonist can be administered to the subject at 48 in a therapeutically effective amount (i.e., in an amount effective to promote neuronal regeneration). Formulations and routes for administering the identified cadherin agonist are described below. For example, the identified cadherin agonist can be delivered to a neuron by directly injecting the cadherin agonist into nervous tissue. Alternatively, the identified cadherin agonist can be indirectly delivered to a neuron by injecting the cadherin agonist via an intravenous route.

Any one or combination of known methods can be used to evaluate in vivo neuronal regeneration. For example, neuronal regeneration can be monitored by observing the progress of symptoms associated with a disease, such as a nervous system injury (e.g., by regaining lost function). Alternatively, neuronal regeneration can be monitored using one or a combination of imaging techniques and/or by detecting the level(s) of polypeptide or polynucleotide expression associated with neuronal regeneration.

Figure 8:
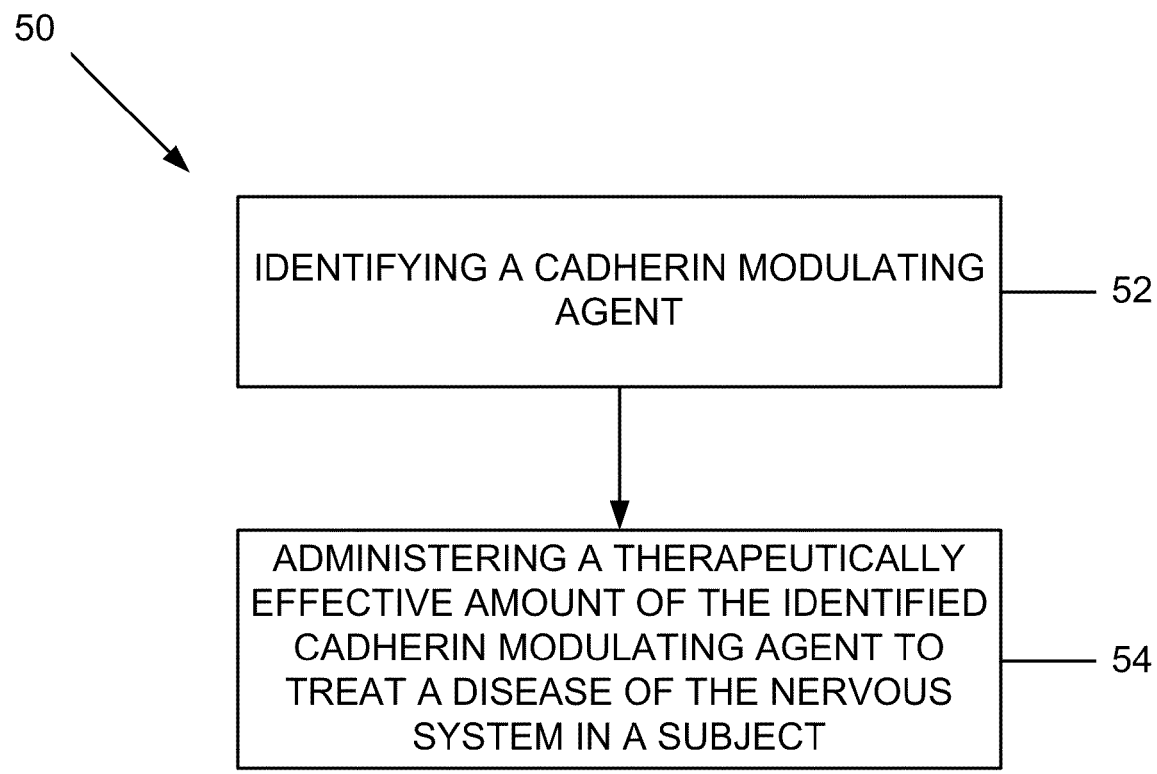
FIG. 8 is a flow diagram illustrating a method for treating an injury of the nervous system in a subject in accordance with another aspect of the present invention.

Another aspect of the present invention is illustrated in FIG. 8. In FIG. 8, a method 50 is provided for treating an injury or disease of the nervous system in a subject. At 52, one step of the method 50 can include identifying a cadherin modulating agent. To identify a cadherin modulating agent, a neurite outgrowth assay can be performed in an identical or similar fashion as illustrated in FIGS. 1-4 and as described above. For example, a neurite outgrowth assay can be performed to determine whether a potential cadherin modulating agent is a cadherin agonist by evaluating neurite outgrowth of at least one neuron disposed on a substrate coated with a cadherin molecule upon application of the cadherin modulating agent to the neuron. Where increased neurite outgrowth as compared to a control is observed, the identified cadherin modulating agent may promote or enhance neurite outgrowth and, thus, be a cadherin agonist. The cadherin agonist could be used to promote neuronal regeneration. In another example, the cadherin modulating agent could be an antagonist that inhibits neurite outgrowth, cell adhesion or migration. The cadherin antagonist could be used to treat neuropathic pain.

At 54, a therapeutically effective amount of the identified cadherin agonist can be administered to the subject. The identified cadherin agonist can be administered to the subject alone or in combination with a physiologically acceptable diluent or pharmaceutically acceptable carrier, such as water or sterile saline. As used herein, the term "pharmaceutically acceptable carrier" refers to any and all solvents, dispersion media, coatings, antibacterial and antifungal agents, isotonic and absorption delaying agents, and the like, compatible with administration of the formulation to a subject. The appropriate carrier will be evident to those skilled in the art and will depend in part upon the route of administration.

Additional components that may be present with the formulation can include adjuvants, preservatives, chemical stabilizers, solvents, and/or other proteins. Typically, stabilizers, adjuvants, and preservatives are optimized to determine the best formulation for efficacy in a subject. Exemplary preservatives can include, but are not limited to, chlorobutanol, potassium sorbate, sorbic acid, sulfur dioxide, propyl gallate, the parabens, ethyl vanillin, glycerin, phenol, and parachlorophenol. Suitable stabilizing ingredients can include, for example, casamino acids, sucrose, gelatin, phenol red, N-Z amine, monopotassium diphosphate, lactose, lactalbumin hydrolysate, and dried milk. Solvents such as dimethyl sulfoxide are commonly used to dilute compounds to improve solubility.

Other components of the formulation can include, for example, surface active substances (e.g., hexadecylamine, octadecylamine, octadecyl amino acid esters, lysolecithin, dimethyl-dioctadecylammonium bromide), methoxyhexadecylglycerol, pluronic polyols, polyamines (e.g., pyran, dextransulfate, poly IC, carbopol), oil emulsions, mineral gels (e.g., aluminum phosphate), liposomes, polysaccharides, lipopolysaccharides, and/or other polymers.

The identified cadherin agonist can be administered using any one or combination of known techniques. Methods of administration can include, but are not limited to, intradermal, intramuscular, intraperitoneal, intravenous, subcutaneous, intranasal, epidural, and oral routes. The identified cadherin agonist may be administered by any convenient route, for example, by infusion or bolus injection, by absorption through epithelial, or by absorption through mucocutaneous linings (e.g., oral mucosa, rectal and intestinal mucosa, etc.). Administration can be systemic or local. For example, the cadherin agonist can be delivered locally via in situ gelling polymers or hydrogels for slow release and local administration. Pulmonary administration can also be employed, e.g., by use of an inhaler or nebulizer and formulation with an aerosolizing agent.

A nervous system injury treatable by the method 50 can include any injury leading to any functional neurological disability as a consequence of neuronal cell death, neuronal tract disorganization, axon degeneration, synapse elimination resulting from any acute or chronic traumatic lesion, any degenerative disease condition, or a combination thereof.

Examples of nervous system injuries can include, but are not limited to, trauma, cerebrovascular disorders (e.g., cerebral hemorrhage, subarachnoid hemorrhage, cerebral infarction, transient (cerebral) ischemic attack (TIA), cerebral arteriosclerosis, Binswanger disease, cerebral sinus thrombosis/cerebral phlebothrombosis, hypertensive encephalopathy, temporal arteritis, transient global amnesia (TGA), moya-moya disease, fibromuscular hyperplasia internal carotid artery/cavernous sinus/fistula, chronic subdural hematoma, amyloid angiopathy, etc.); circulatory disorder of the spinal cords (e.g., spinal infarct, transient spinal ischemia, spinal hemorrhage, circulatory deformity of the spinal cord, spinal subarachnoid hemorrhage, subacute necrotizing myelitis, etc.); infective and inflamational disorders (e.g., meningitis, encephalitis, Herpes simplex encephalitis (HSE), Japanese encephalitis, other encephalitises, rabies, slow virus disease (e.g., subacute sclerosing panencephalitis (SSPE), progressive multiforcal leukoencephalitis (PML), Creutzfeldt-Jakob disease (CJD), etc.), neural Behcet disease, chorea minor AIDS dementa syndrome, neuro syphilis, cerebral abscess, spinal epidural abscess, HTLV-1-associated myelopathy (HAM), poliomyelitis); demyelining diseases (multiple sclerosis (MS), acute disseminated encephalomyelitis (ADEM), Balo's concentric sclerosis, inflammatory universal sclerosis, leukodystrophy, metachromatic leukodystrophy, Krabbe's disease, adrenoleukodystrophy (ALD), Canavan's disease (leukodystrophy), Pelizaeus-Merzbacher disease (leukodystrophy), Alexander's disease (leukodystrophy), etc.); dementia disease (Alzheimer's disease, senile dementia of Alzheimer type (SDAT), Pick's disease, cerebrovascular dementia, Creutzfeldt-Jakob disease (CJD), Parkinson-dementia complex, normal pressure hydrocephalus, progressive supranuclear palsy (PSP), etc.); basal nuclei degenerative disease (e.g., Parkinson disease (PD), symptomatic parkinsonism, striatonigral denegeration (SNG), Parkinson-dementia complex, Huntington's disease (HD), essential tremer, athetosis, dystonia syndrome (e.g., idiopathic torsion distonia, local dystonia (spasmodic wryneck, writer's cramp, Meige's disease, etc.), symptomatic dystonia (Hallervorden-Spats disease, drug-induced dystonia, etc.), Gilles de la Tourette's syndrome, etc.); spinocerebellar degenerative disease (e.g., spinocerebellar degeneration (SCD)(Shy-Drager syndrome, Machado-Joseph disease (MJD), etc.), Louis-Bar syndrome, Bassen-Kornzweig syndrome, Refsum disease, other cerebellar ataxias, etc.); motor neuron diseases (MND) (e.g., amyotrophic lateral sclerosis (ALS), progressive bulbar amytrophy (see amyotrophic lateral sclerosis), familial amyotrophic lateral sclerosis, Werdnig-Hoffmann disease (WHD), Kugelberg-Welander (K-W) disease, bulbar spinal sclerosis, juvenile one upper limb muscular sclerosis, etc.); tumor diseases of brain and spinal cord (e.g., intracranial tumor, spinal abscess, meningeal carcinoma, etc.); functional diseases (e.g., epilepsy, chronic headache, syncope (see syncope), idiopathic endocranial increased intracranial pressure disease, Meniere disease, narcolepsy, Kleine-Levin syndorome, etc.); toxic and metabolic diseases (e.g., drug intoxication (phenothiazines-derived antipsychotic agent intoxication, sedatives and hypnotics intoxication, antibiotics intoxication, antiparkinson drug, antitumor drug intoxication, β-blocker intoxication, calcium antagonist intoxication, clofibrate intoxication, antiemetic drug intoxication, SMON disease, salicylic acid intoxication, digitalis intoxication, narcotic addiction, etc.), chronic alcoholism (Wernicke encephalopathy, Marchiafava-Bignami syndrome, central pontine myelinolysis, etc.), organic solvent poisoning and pesticide poisoning (e.g., organophosphate compounds poisoning, carbamates poisoning, chloropicrin poisoning, paraquat poisoning, etc.), organophosphate nerve gas poisoning, carbon monooxide poisoning, hydrogen sulfide poisoning, cyanide compound poisoning, mercurial poisoning (metallic mercurial poisoning, inorganomercurial poisoning, organomercurial poisoning, etc.), lead poisoning, tetraethyl lead poisoning, arsenic poisoning, cadmium poisoning, chrome poisoning, manganese poisoning, metal fume fever, sedatives and hypnotics intoxication, salicylic acid intoxication, digitalis intoxication, narcotic addiction, food poisoning (e.g., natural food poisoning (tetradotoxin poisoning, measles shell fish poison food poisoning, diarrhogenic shell fish poison food poisoning, ciguatera, mushroom poisoning, potato-plant poisoning, etc.), vitamin deficiency (vitamin A deficiency, vitamin B1 deficiency, vitamin B2 deficiency, pellagra, scurvy, vitamin dependency), lipidosis, Gaucher disease, Niemann-Pick disease, etc.), acquired disorders of amino acid metabolism, Wilson disease, amyloidosis, etc.); congenital deformity (Arnold-Chiari malformation, Klippel-Feil syndrome, basilar impression, syringomyelia); neurosis and dermatopathy (e.g., phacomatosis, von-Recklinghausen, tuberous sclerosis, Sturge-Weber, von Hippel Lindau, etc.); spinal diseases (deformity of the spine herniated intervertebral discs, lateral axial band osteosis, etc.); and retinal diseases, such as retinal degeneration, retinal dystrophies, retinal detachment, retinitis pigmentosa, retinoblastoma, diabetic retinopathy, macular degeneration, glaucoma, and the like.

Administration of the identified cadherin agonist can enhance neurite outgrowth and/or neuronal regeneration in the subject. Any one or combination of known methods can be used to evaluate in vivo neurite outgrowth and/or neuronal regeneration. For example, the amount of neurite outgrowth and/or neuronal regeneration can be monitored by observing the progress of symptoms associated with the nervous system injury, by directly observing neurite outgrowth and/or neuronal regeneration in vivo using one or a combination of imaging techniques, and/or by detecting the levels of polypeptide or polynucleotide expression associated with neuronal regeneration and/or neurite outgrowth. By administering a therapeutically effective amount of the identified cadherin agonist to the subject, the subject may be able to regain partial or entire nervous system function.

Figure 9:
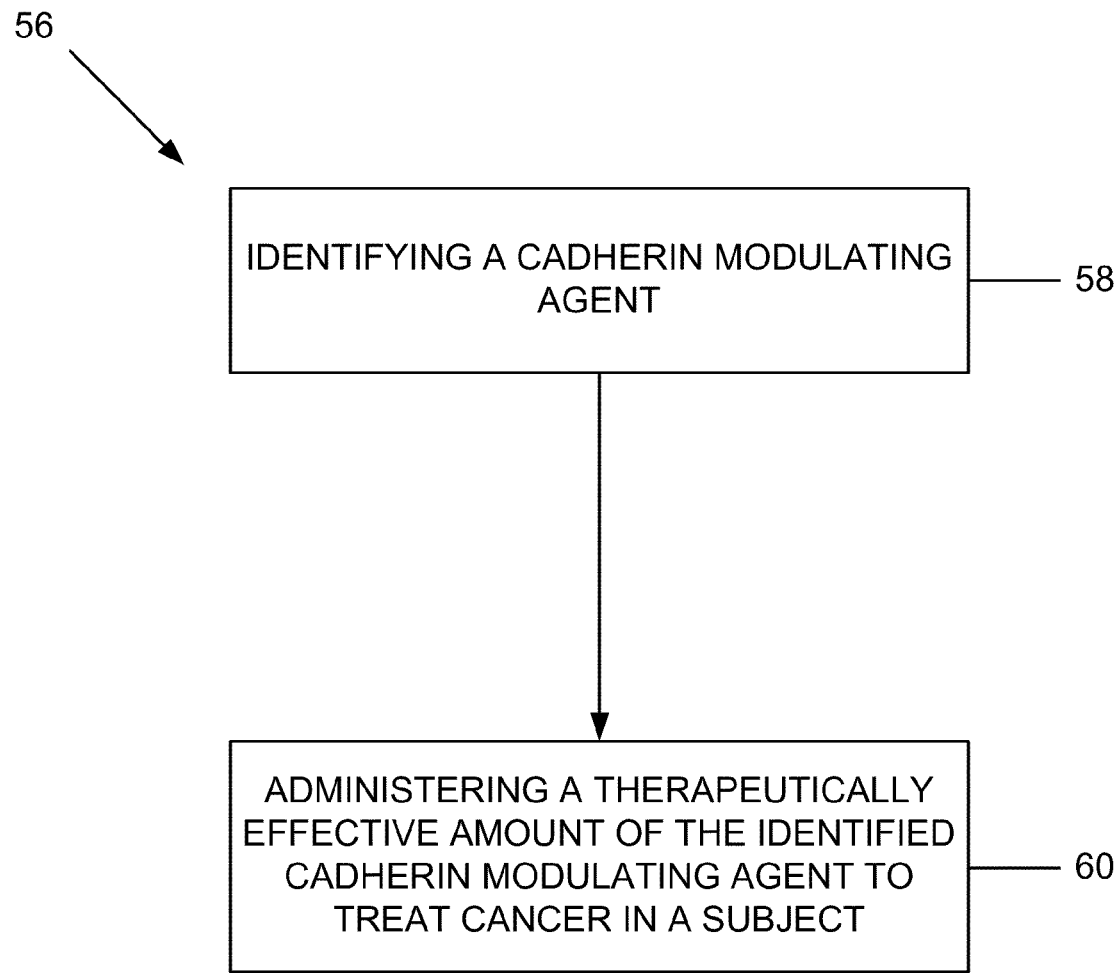
FIG. 9 is a flow diagram illustrating a method for treating cancer in a subject in accordance with another aspect of the present invention.

Another aspect of the present invention is illustrated in FIG. 9. In FIG. 9, a method 56 is provided for treating cancer in a subject. The method 56, at step 58, can include identifying a cadherin modulating agent. To identify the cadherin modulating agent, a neurite outgrowth assay can be performed in an identical or similar fashion as illustrated in FIGS. 1-4 and as described above. For example, a neurite outgrowth assay can be performed to determine whether a potential cadherin modulating agent is a cadherin agonist or a cadherin antagonist by evaluating neurite outgrowth of at least one neuron disposed on a substrate coated with a cadherin molecule upon application of the cadherin modulating agent to the neuron. In one example, a cadherin modulating agent may be capable of treating cancer in the subject if: (1) the cadherin modulating agent increases neurite outgrowth on an E-cadherin coated substrate by at least about 101% as compared to a control (e.g., E-cadherin agonist); (2) the cadherin modulating agent increases neurite outgrowth on an E-cadherin coated substrate by at least about 120% as compared to a control (e.g., E-cadherin agonist); (3) the cadherin modulating agent decreases neurite outgrowth on an N-cadherin coated substrate by at least about 40% as compared to a control (e.g., N-cadherin antagonist); or (4) the cadherin modulating agent decreases neurite outgrowth on an N-cadherin coated substrate by at least about 50% as compared to a control (e.g., N-cadherin antagonist). Other combinations of cadherin agonists and antagonists are also envisioned to be therapeutically effective.

At 60, a therapeutically effective amount of the identified cadherin modulating agent can be administered to the subject individually or in combination. The identified cadherin modulating agent can be administered to the subject alone or in combination with a physiologically acceptable diluent or pharmaceutically acceptable carrier, such as water or sterile saline (as described above). Additionally, the identified cadherin modulating agent can be administered to the subject in an amount and via a route as described above. For example, a therapeutically effective amount of a pharmaceutical composition comprising the identified cadherin modulating agent can be administered to the subject via an intravenous route using a hypodermic needle or intravenous drip line.

Cancers treatable by the method 56 can include any condition characterized by an increase in the number of abnormal cells derived from a given normal tissue, invasion of adjacent tissues by these abnormal cells, or lymphatic or blood-borne spread of malignant cells to regional lymph nodes and to distant sites (metastasis). The term "cancer" can also include all types of neoplasm or malignant or benign tumors found in mammals, including carcinomas and sarcomas. Examples of cancers can include cancer of the brain (e.g., brain tumors), breast, pancreas, cervix, colon, prostate, testes, bone, head and neck, kidney, lung, non-small cell lung, melanoma, mesothelioma, ovary, leukemia, carcinoma, sarcoma, stomach, uterus and medulloblastoma.

Leukemias treatable by the method 56 can generally include progressive, malignant diseases of the blood-forming organs characterized by distorted proliferation and development of leukocytes (and their precursors) in the blood and bone marrow. Leukemia is generally clinically classified on the basis of: (1) the duration and character of the disease (i.e., acute or chronic); (2) the type of cell involved (i.e., myeloid (myelogenous), lymphoid (lymphogenous), or monocytic); and (3) the increase or non-increase in the number abnormal cells in the blood (i.e., leukemic or aleukemic). Non-limiting examples of leukemia can include acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

Sarcomas treatable by the method 56 can generally include tumors comprised of closely packed cells embedded in a fibrillar or homogeneous substance. Non-limiting examples of sarcomas can include chondrosarcoma, cholangiosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, soft-tissue sarcoma, synovial sarcoma, and telangiectaltic sarcoma.

Melanomas treatable by the method 56 can generally include tumors arising from the melanocytic system of the skin and other organs. Non-limiting examples of melanomas can include acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

Carcinomas treatable by the method 56 can generally include any malignant new growth comprised of epithelial cells tending to infiltrate the surrounding tissues and give rise to metastases. Non-limiting examples of carcinomas can include acinar carcinoma, acinous carcinoma, adenocystic carcinoma, adenoid cystic carcinoma, breast carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bladder carcinoma, bronchioalveolar carcinoma, bronchiolar carcinoma, bronchogenic carcinoma, cerebriform carcinoma, cholangiocellular carcinoma, chorionic carcinoma, colloid carcinoma, colo-rectal carcinoma, cervical carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gastric carcinoma, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lung carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, ovarian carcinoma, pancreatic carcinoma, prostatic carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, testicular carcincoma, transitional cell carcinoma, thyroid carcinoma, carcinoma tuberosum, tuberous carcinoma, verrucous carcinoma, and carcinoma villosum.

Other non-limiting examples of cancers treatable by the method 56 can include head and neck squamous cell carcinoma (eye, lip, oral, pharynx, larynx, nasal, carcinoma of the tongue, and esophogeal carcinoma), melanoma, squamous cell carcinoma (epidermis), glioblastoma, astrocytoma, oligodendroglioma, oligoastrocytoma, meningioma, neuroblastoma, rhabdomyosarcoma, soft-tissue sarcomas, osteosarcoma, hematologic malignancy at the CNS site, breast carcinoma (ductal and carcinoma in situ), thyroid carcinoma (papillary and follicular), lung carcinoma (bronchioloalveolar carcinoma, small cell lung carcinoma, mixed small cell/large cell carcinoma, combined small cell carcinoma, non-small cell lung carcinoma, squamous cell carcinoma, large cell carcinoma, and adenocarcinoma of the lung), hepatocellular carcinoma, colo-rectal carcinoma, cervical carcinoma, ovarian carcinoma, prostatic carcinoma, testicular carcinoma, gastric carcinoma, pancreatic carcinoma, cholangiosarcoma, lymphoma (Hodgkin's and non-Hodgkin's types of T- and B-cell origin), and bladder carcinoma.

In one example of the method 56, a subject may be suffering from a primary tumor. In this case, a therapeutically effective amount of a cadherin agonist, such as an E-cadherin agonist can be administered to the subject via an intra-tumoral or intravenous route. Upon administration of the E-cadherin agonist, tumorigenesis in the subject may be reduced or inhibited. In another example of the method 56, a subject may be suffering from a metastatic mammary tumor. In this case, a therapeutically effective amount of a cadherin antagonist, such as an N-cadherin antagonist or a Cadherin-11 antagonist can be administered to the subject via an intra-tumoral or intravenous route. Upon administration of the N-cadherin antagonist and/or the Cadherin-11 antagonist, tumorigenesis in the subject may be reduced or inhibited. In a further example of the method 56, a subject may be suffering from cancer and a therapeutically effective amount of E-cadherin agonist and a N-cadherin antagonist or a Cadherin-11 antagonist can be administered to the subject via an intra-tumoral or intravenous route. Upon administration of the E-cadherin agonist and N-cadherin antagonist and/or the Cadherin-11 antagonist, cancer in the subject may be reduced or inhibited.

Another aspect of the present invention includes a method for treating neuropathic pain in a subject. One step of the method can include identifying a cadherin antagonist. To identify the cadherin antagonist, a neurite outgrowth assay can be performed in an identical or similar fashion as illustrated in FIGS. 1-4 and described above. For example, a neurite outgrowth assay can be performed to determine whether a potential cadherin antagonist reduces or inhibits neurite outgrowth of at least one neuron disposed on a substrate coated with a cadherin molecule upon application of the cadherin antagonist to the neuron. A cadherin antagonist may be capable of treating neuropathic pain in the subject if: (1) the cadherin antagonist decreases neurite outgrowth by at least about 40% as compared to a control; or (2) the cadherin antagonist decreases neurite outgrowth by at least 50% as compared to a control.

A therapeutically effective amount of the identified cadherin antagonist can be administered to the subject. The identified cadherin antagonist can be administered to the subject alone or in combination with a physiologically acceptable diluent or pharmaceutically acceptable carrier, such as water or sterile saline (as described above). Additionally, the identified cadherin antagonist can be administered to the subject in an amount and via a route as described above. For example, a therapeutically effective amount of a pharmaceutical composition comprising the identified cadherin antagonist can be administered to the subject via an intravenous route using a hypodermic needle or intravenous drip line.

Neuropathic pain treatable by the method can include any abnormal state of pain sensation in which a reduction of pain threshold is continued due to functional abnormalities accompanying damage or degeneration of a nerve, plexus, or perineural soft tissue caused by a wound (e.g., laceration, contusion, nerve avulsion injury, amputation of a limb), compression (e.g., carpal tunnel syndrome, trigeminal neuralgia, tumor activity), infection, cancer, ischemia, and/or metabolic disorder (e.g., diabetes mellitus).

Other examples of neuropathic pain treatable by the method can comprise diseases of the nerves (primary neuropathy) and neuropathy caused by systemic disease (secondary neuropathy) including, but not limited to, diabetic neuropathy, Herpes Zoster (shingles)-related neuropathy, uraemia-associated neuropathy, amyloidosis neuropathy, HIV sensory neuropathies, hereditary motor and sensory neuropathies (HMSN), hereditary sensory neuropathies (HSNs), hereditary sensory and autonomic neuropathies, hereditary neuropathies with ulcero-mutilation, nitrofurantoin neuropathy, tumaculous neuropathy, neuropathy caused by nutritional deficiency, neuropathy caused by kidney failure, allodynia (i.e., a pain sensation induced by mechanical or thermal stimulus that usually does not normally provoke pain), hyperalgesia (i.e., an excessive response to a stimulus that is normally painful), hyperesthesia (i.e., an excessive response to a contact stimulus), diabetic polyneuropathy, entrapment neuropathy, cancer pain, central pain, labor pain, myocardial infarction pain, post-stroke pain, pancreatic pain, colonic pain, muscle pain, post-operative pain, pain associated with Parkinson's disease, pain associated with intensive care, pain associated with a periodontal disease (e.g., gingivitis, periodontitis), menstrual pain, migraine pain, persistent headaches (e.g., cluster headache or chronic tension headache), persistent pain states (e.g., fibromyalgia or myofascial pain), post-therapeutic neuralgia, bursitis, pain associated with multiple sclerosis, pain due to spinal trauma and/or degeneration, burn pain, referred pain, and pain associated with inflammatory conditions (e.g., arthritis, neuritis, myositis, colitis).

The following example is for the purpose of illustration only and is not intended to limit the scope of the claims, which are appended hereto.

EXAMPLE 1

E-cadherin Promotes Neurite Outgrowth

Figure 10:
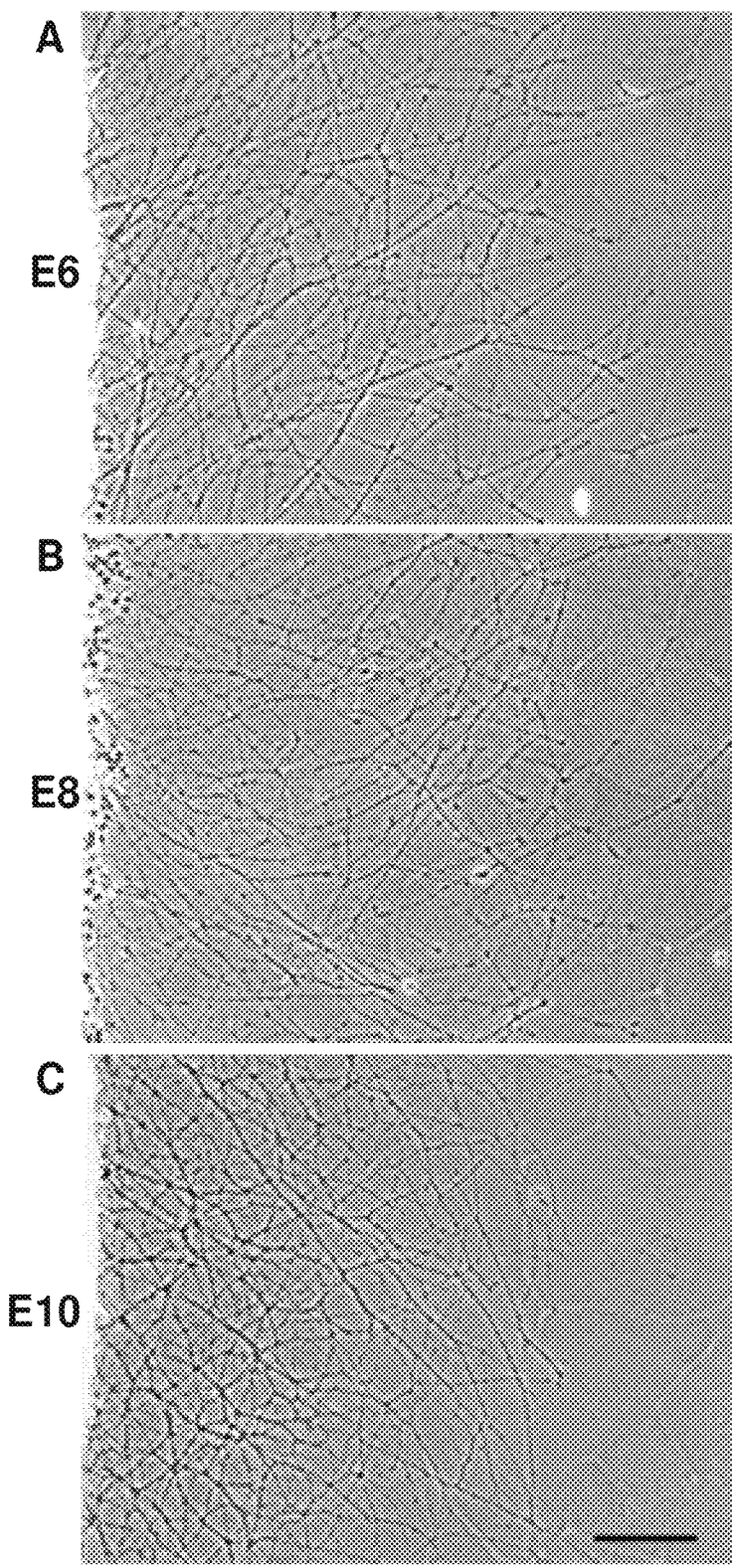
FIGS. 10A-C are a series of images showing that E-cadherin promotes RGC neurite outgrowth at various stages of development. E6 (FIG. 10A), E8 (FIG. 10B) and E10 (FIG. 10C) chick retinal explants were isolated and cultured on an E-cadherin substrate for 20 hours. Scale bar, 200 μm.
Figure 13:
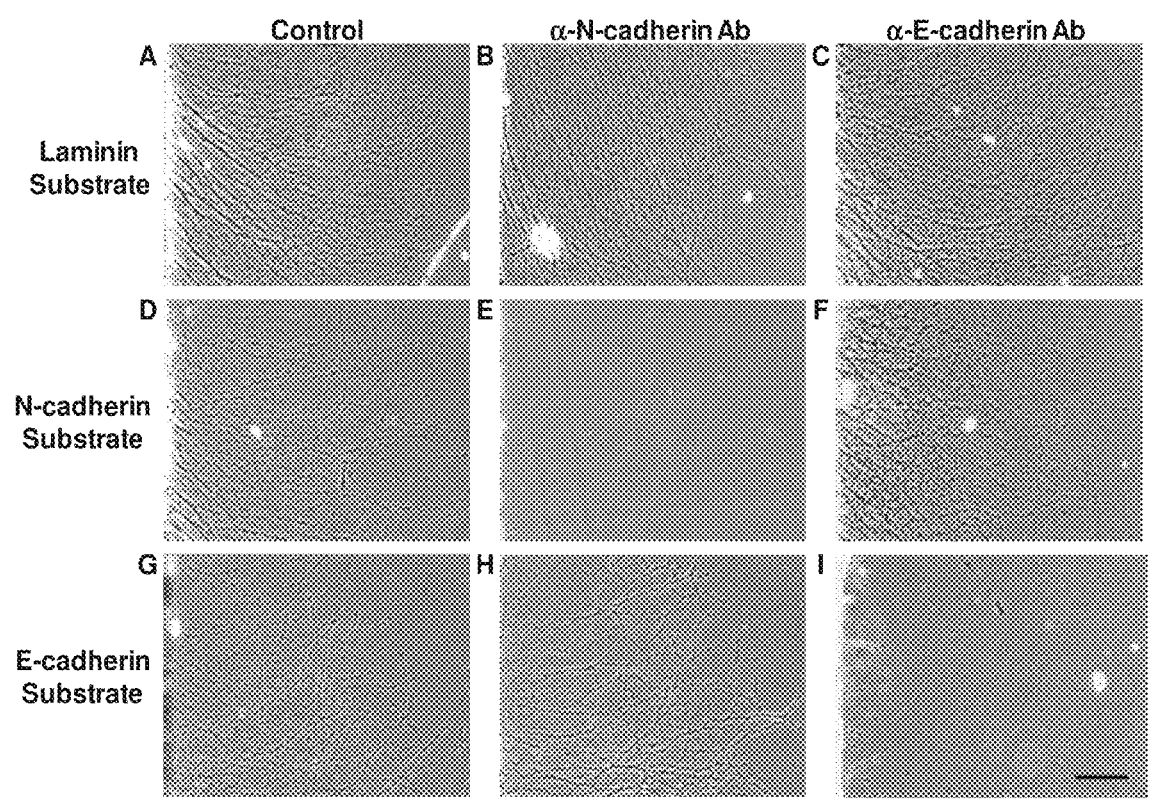
FIGS. 13A-I are a series of images showing E-cadherin-mediated neurite outgrowth is specifically blocked by E-cadherin adhesion blocking antibodies. Retinal explants from E8chick embryos were cultured on a laminin (FIG. 13A-C), N-cadherin (FIG. 13D-F) or E-cadherin (FIGS. 13G-I) substrate in the presence of adhesion blocking antibodies to N-cadherin (FIG. 13B, FIG. 13E, FIG. 13H) or E-cadherin (FIG. 13C, FIG. 13F, FIG. 13I). Antibodies against N-cadherin inhibited neurite outgrowth on an N-cadherin (FIG. 13E) substrate, whereas they had no effect on neurite outgrowth on laminin (FIG. 13B) or E-cadherin (FIG. 13H) substrates. Similarly, antibodies against E-cadherin inhibited neurite outgrowth on an E-cadherin (FIG. 13I) substrate, while they had no effect on neurite outgrowth on laminin (FIG. 13C) or N-cadherin (FIG. 13F) substrates. Scale bar, 200 μm.

Early in embryogenesis, one or two leading RGC axons migrate along the optic stalk toward the optic tectum (Mey and Thanos, *Brain Res Brain Res Rev.* 35:205-245, 2001). As development continues, successive waves of axons project along the neuronal and glial cells within the optic nerve (Mey and Thanos, *Brain Res Brain Res Rev.* 35:205-245, 2001). Thus, cadherins expressed on the surface of these cells can serve as a "substrate" for axonal migration. To determine whether E-cadherin promotes neurite outgrowth, we used a well-established in vitro model to investigate neurite outgrowth (Lagenaur and Lemmon, *PNAS* 84:7753-7757, 1987; Burden-Gulley and Brady-Kalnay, *J Cell Bio.* 144:1323-1336, 1999). Purified E-cadherin was coated on tissue culture dishes and used as a substrate to culture tissue explants. Neurite outgrowth on an E-cadherin substrate was observed from retinal explants taken at E6, E8 and E10, after 20 hours in culture (FIGS. 10A-C). Neurite length and density was similar between all time points examined, suggesting that E-cadherin is equally effective at promoting neurite outgrowth at these ages. Neurite outgrowth on E-cadherin was similar in length and density to that observed on N-cadherin (FIGS. 13D and 13G).

Figure 11:
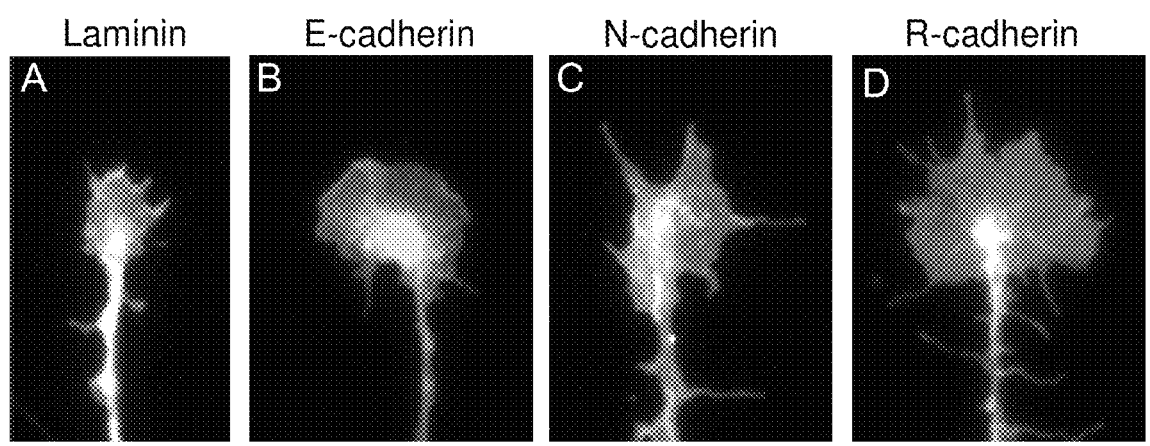
FIGS. 11A-C are a series of DiI-labeled micrographs demonstrating that growth cones on a laminin substrate (FIG. 11A) appear to have small lamellipodia with few, short filopodia. On an E-cadherin substrate (FIG. 11B), growth cones have very large, broad lamellipodia with short filopodial processes. Growth cones on an N-cadherin substrate (FIG. 11C) have larger lamellipodia in addition to short filopodial processes. Growth cones on R-cadherin have a hybrid morphology with both filopodia and a broad lamellipodia (FIG. 11D). Scale bar, 10 μm.

Growth cones located at the distal tip of the axon allow neurons to interact with the extracellular environment. Each growth cone recognizes cues in the extracellular environment and on the surface of adjacent cells via membrane-associated proteins such as the cadherins (Hirano et al., *Front Biosci.* 8:d306-355, 2003; Kiryushko et al., *Ann NY Acad. Sci.* 1014:140-154, 2004). These interactions lead to intracellular signaling events, which induce cytoskeletal rearrangements that ultimately regulate axon guidance. DiI labeling of RGCs illustrates that the morphology of the growth cones present on an E-cadherin substrate consists of large, broad lamellipodia with a few short filopodia (FIG. 11C). In contrast, growth cones on N-cadherin had smaller lamellipodia with several short filopodial processes (FIG. 11B), which is consistent with previous published work (Bixby and Zhang, *J Cell Biol.* 110:1253-1260, 1990; Payne et al., *Cell Motil Cytoskeleton* 21:65-73, 1992). Growth cones with small lamellipodia were observed on laminin (FIG. 11A). Growth cones on R-cadherin have a hybrid morphology with both filopodia and a broad lamellipodia (FIG. 11D). The differences in growth cone morphology observed on each cadherin substrate suggest that distinct signaling mechanisms may be involved in E-cadherin versus N-cadherin-dependent neurite outgrowth.

Figure 12:
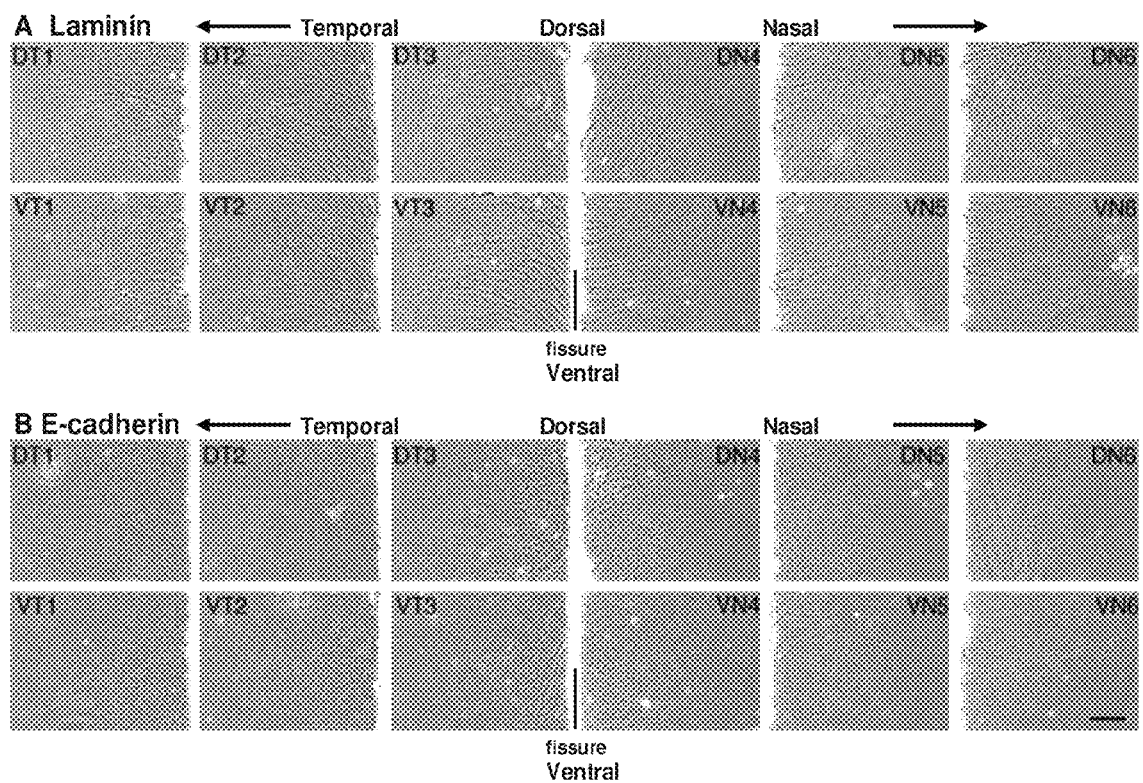
FIGS. 12A-B are a series of images showing neurite outgrowth on E-cadherin and laminin is independent of RGC cell body origin. Explants from E8 chick retina were cut parallel to the optic fissure and explants from retina were cultured on E-cadherin (FIG. 12B) or laminin (FIG. 12A) substrates. Images were acquired after 20 hours in culture from a location corresponding to the outer third of each explant. Each number indicates the explant number (e.g., 1 and 6 are most peripheral). Dorsal (D), ventral (V), nasal (N), temporal (T). Scale bar, 200 μm.

The 3-dimensional position of the RGC cell body within the retina determines which positional cues the RGC cell body and therefore its axon will respond to. Previous studies have shown that at E8, N-cadherin-mediated neurite outgrowth predominantly occurs from RGCs originating from the ventral-nasal, ventral-temporal and dorsal-temporal retina while little to no growth occurs from RGCs from the dorsal-nasal region (Burden-Gulley et al., *J Neurosci.* 22:3615-3627, 2002). In order to identify which regions of the retina promote neurite outgrowth on an E-cadherin substrate, explants from distinct regions of the retina were isolated and cultured in vitro. In contrast to N-cadherin, robust neurite outgrowth on E-cadherin was observed from all regions of the retina (FIG. 12B). Laminin, which has been shown to promote robust neurite outgrowth from all regions of the retina (Burden-Gulley et al., *J Neurosci.* 22:3615-3627, 2002), was used as a control (FIG. 12A).

Classical cadherins are predominantly homophilic binding proteins (Ivanov et al., *Biochemistry (Mosc)* 66:1174-1186, 2001; Gooding et al., *Bioessays* 26:497-511, 2004). To confirm that neurite outgrowth on E- or N-cadherin substrates is specific, E8 retinal explants were cultured on an E-cadherin, N-cadherin or laminin substrate in the presence or absence of adhesion-blocking antibodies. Neurite outgrowth on an E-cadherin substrate was blocked when cultured in the presence of antibodies against the extracellular domain of chick E-cadherin (FIG. 13I). These E-cadherin blocking antibodies had no effect on N-cadherin-mediated outgrowth (FIG. 13F). Antibodies against the extracellular domain of chick N-cadherin (Hatta and Takeichi, Nature 320:447-449, 1986) had no effect on E-cadherin-mediated neurite outgrowth (FIG. 13H). However, N-cadherin adhesion blocking antibodies did block neurite outgrowth on an N-cadherin substrate (FIG. 13E). Neurite outgrowth on laminin was unaffected by E- and N-cadherin adhesion blocking antibodies (FIGS. 13B-C). Taken together, these data suggest that neurite outgrowth on an E-cadherin substrate is due to specific E-cadherin binding.

Figure 14:
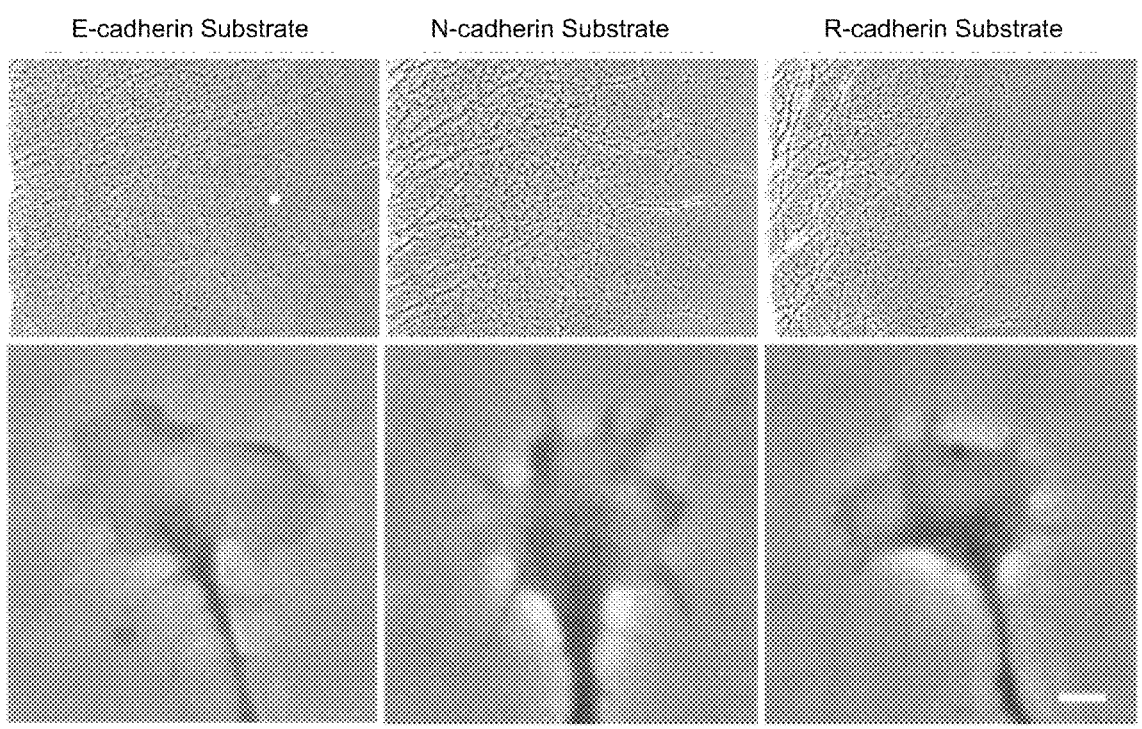
FIG. 14 is a series of photographs showing neurite outgrowth of retinal neurons and growth cone morphology on N-, E- and R-cadherin. The images below the neurite outgrowth shows typical growth cone morphology on the substrate listed at the top.

E-, N- and R-cadherin promote neurite outgrowth of retinal ganglion cells (RGCs). Phase contrast images of RGC growth cones on various cadherin substrates display unique morphologies. RGC growth cones on an E-cadherin substrate have very large, broad lamellipodia with very few filopodial processes (FIG. 14). Growth cones on an N-cadherin substrate appear to have small lamellipodia with several filopodial processes (FIG. 14). Growth cones on an R-cadherin substrate have moderately broad lamellipodia with several short filopodia (FIG. 14).

Figure 15:
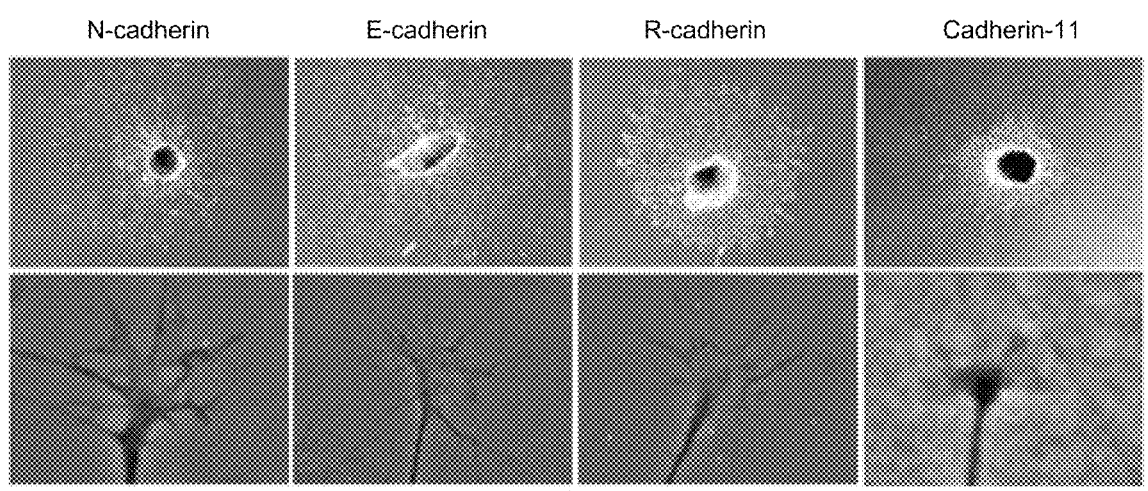
FIG. 15 is a series of photographs showing neurite outgrowth of DRG neurons and growth cone morphology on N-, E- and R-cadherin as well as Cadherin-11. The image below the neurite outgrowth shows typical growth cone morphology on the substrate listed at the top.

Neurite outgrowth assays were performed with Dorsal Root Ganglion neurons. N-, E-, R-cadherin and Cadherin-11 promote outgrowth of DRG neurons. DRG growth cones display distinct morphologies on the cadherin substrates (FIG. 15). The growth cones on N-cadherin, E-cadherin and R-cadherin are similar to RGCs. Growth cones on a Cadherin-11 substrate have large, broad lamellipodia (FIG. 15).

Neurite Outgrowth Assays

E-cadherin, N-cadherin and R-cadherin were either purified or obtained from R&D Systems (Minneapolis, Minn.). Briefly, 35 mm tissue culture dishes were coated with nitrocellulose in methanol (Lagenaur and Lemmon, *PNAS USA* 84:7753-7757, 1987) and allowed to dry. Several different lots of substrate were used over the course of the experiments resulting in variability in the concentration of substrate used. 0.25-0.50 µg of E-cadherin, 0.06-0.15 µg of N-cadherin or 2.50-4.00 µg of laminin was spread across the center of each dish and incubated for 20 minutes at room temperature. Remaining binding sites on the nitrocellulose were blocked with 2% BSA in CMF, and the dishes were rinsed with RPMI 1640 medium (Hyclone, Logan, Utah).

Embryonic day 8 (stage 32-33 according to Hamburger and Hamilton, *J Morphol.* 88:49-92, 1951) chick eyes were dissected in cold CMF and the retinal explants were prepared as described (Halfter et al., *Dev Biol.* 95:56-64, 1983; Drazba and Lemmon, *Dev Biol.* 138:82-93, 1990; Burden-Gulley and Brady-Kalnay, *J Cell Biol.* 144:1323-1336, 1999). Briefly, neural retinas were flattened on concavalin-coated nitrocellulose filters and cut into 350 µm-wide explants. Explants were placed retinal ganglion side down onto substrate coated dishes and cultured in RPMI-1640, 10% fetal bovine serum (Hyclone), 2% chick serum (Invitrogen, Carlsbad, Calif.), 100 U/ml penicillin, 0.1 mg/ml streptomycin, 0.025 µg/ml amphotericin (Sigma).

For growth cone visualization, Lab-TekII Chamber Slides (Fisher Scientific) were coated with 0.01% poly-L-lysine overnight, rinsed 5× with distilled $H_2O$ and allowed to dry overnight. The slides were then coated with E-cadherin, N-cadherin, R-cadherin or laminin substrate as described above. Retinas were prepared as described above. The explant was placed retinal ganglion side down onto the substrate coated slide. DiI crystals (Invitrogen) were placed on the tissue. Culture medium containing serum was then added and explants were incubated for 20 hours. The growth cones were imaged with phase or fluorescence optics.

For antibody inhibition studies, N-cadherin blocking antibody, NCD2 (Hatta and Takeichi, *Nature* 320:447-449, 1986) at a final concentration of 11 µg/ml, or E-cadherin blocking antibody, goat anti-L-CAM (chick E-cadherin) (Renaud-Young and Gallin, *J Biol. Chem.* 277:39609-39616, 2002) at a final concentration of 1 mg/ml. The goat anti-L-CAM (chick E-cadherin) antibody was a kind gift from Drs. Bruce Cunningham and Warren Gallin. The antibodies were added to the culture media in each substrate-coated culture dish and incubated at room temperature for 30 minutes prior to addition of the explant. Explants were incubated for 20 hours in the presence of the blocking antibody.

Cadherin modulating agents were resuspended with either culture medium or Dimethylsulfoxide (DMSO) to make stock solutions at a final concentration of 1-10 mM. Working solutions were prepared by diluting the stock solutions into the culture medium to final concentrations of 10-100 µM. Control stock solutions were made using either medium alone or DMSO diluted into medium at a concentration matched to the cadherin modulating agent stock solutions.

Dorsal root ganglion (DRG) explant cultures were prepared using embryonic day 7 (stage 29-30) chicks. The chicks were eviscerated, laminectomized and the DRGs from lumbosacral levels 1-8 were removed and transferred to cold Calcium-Magnesium free Hank's buffer (CMF). The surrounding connective tissue and nerve roots were removed, and each DRG was divided in half with forceps. DRG halves were transferred to substrate coated tissue culture dishes containing 650 µl of DRG plating medium (DMEM/F12 medium containing 2% Chick Serum, 2% Fetal Bovine Serum, 40 µg/ml Conalbumin, 1.2 µg/ml Ascorbic Acid, 0.2 IU/ml Insulin, 200 µM Glutamine, 0.05 ng/ml Nerve Growth Factor, Penicillin-Streptomycin-Fungizone) and incubated in a humidified chamber at 37° C., 5% $CO_2$ for 20 hours to facilitate attachment to the substrate. An additional 1 ml of plating medium containing control or cadherin modulating agent was added to each dish and the dishes incubated further for a total incubation of 43-45 hours. Cultures were fixed and analyzed for effects of the cadherin modulating agent on neurite outgrowth.

Quantitation of Neurite Outgrowth

Neurite outgrowth from specific regions of the retina was analyzed using a SPOT RT digital camera and image acquisition software (Diagnostic Instruments, Inc., Sterling Heights, Mich.). In short, the length of the five longest neurites per given area of the explant were measured perpendicular to the explant tissue. To calculate neurite density, images were analyzed using Metamorph software version 6.3r4 (Universal Imaging, Downington, Pa.). The data from all similar experiments were combined, analyzed by Student's t test and graphed (Microsoft Excel, 10.0.0 2001).

EXAMPLE 2

We screened a library of more than 300 peptidomimetic small molecules, which have a three-dimensional structure that is similar to a cyclic peptide (ADH-1) that comprises the cadherin cell adhesion recognition sequence HAV. We evaluated the ability of these peptidomimetic small molecules to modulate two distinct N-cadherin-mediated cellular activities: cell migration, as assayed by retinal ganglion cell (RGC) neurite outgrowth, and cell adhesion, as evaluated by human LN-229 glioblastoma cell adhesion assays. Our experiments identified 21 small molecule antagonists of N-cadherin-mediated neurite outgrowth, which we then classified into three groups according to their level of inhibition: strong, intermediate and weak. The strong antagonists of neurite outgrowth were also strong antagonists of N-cadherin-mediated adhesion of human glioblastoma cells.

N-Cadherin Sequence Analysis

Amino acid sequences of N-cadherin were obtained through PubMed's protein database (NCBI), using the following protein accession numbers: CAA40773.1 for *Homo sapiens*' sequence, NP_112623.1 for *Rattus norvegicus*, NP_031690.3 for *Mus musculus*, and NP_001001615.1 for *Gallus gallus* (chick). The structure of ADH-1 is based on one published by Williams et al. 2000.

Generation of N-Cadherin Small Molecule Antagonists

Peptidomimetic small molecules were identified based on structural similarity to the peptide or cyclic peptide containing the classical cadherin cell adhesion recognition sequence HAV, N-Ac-CHAVC-$NH_2$, (SEQ ID NO: 3) as described in U.S. Pat. No. 7,446,120 B2. In brief, peptidomimetics were identified by Adherex from two large databases of three-dimensional structures, the National Cancer Institute (NCI) 3D-database and the Available Chemicals Directory (MDL Information Systems, San Leandro, Calif.). Using the Chem-X program (Oxford Molecular Group, PLC; Oxford, England), the 3D structures obtained from these databases were searched by Adherex for similarities in the critical distances in the low energy conformation of N-Ac-CHAVC-$NH_2$ (SEQ ID NO: 3). The critical features of N-Ac-CHAVC-$NH_2$ (SEQ ID NO: 3) are the nitrogen atoms on the imidazole ring and the hydrophobic portion of the valine residue (U.S. Pat. No. 7,446,120 B2, column 30). Based on the distances between these critical features of the low energy conformation of N-Ac-CHAVC-$NH_2$, a number of queries were generated and allowed distance bit screening of the 3D databases to identify peptidomimetics. The compounds were further determined by Adherex to have the correct sub-structural and conformational similarities to N-Ac-CHAVC-$NH_2$. A list of compounds identified by this method is provided in U.S. Pat. No. 7,446,120 B2, FIG. 15A-15BG. We screened derivatives of those described compounds in our neurite outgrowth and adhesion assays.

Culture of Retinal Explants

Sterile 35 mm tissue culture dishes for retinal explants were coated with nitrocellulose in methanol and allowed to dry, before spreading 0.04-0.045 μg/plate of human N-cadherin-Fc (R&D Systems, Minneapolis, Minn.) across the center of each dish. Remaining binding sites on the nitrocellulose were blocked with 2% bovine serum albumin (BSA; Sigma, St. Louis, Mo.) in calcium/magnesium free phosphate buffer (CMF), and the dishes were rinsed with RPMI-1640 medium (HyClone, Logan, Utah). Cultures of retinal explants from embryonic day 8 chick were made as previously described in. Retinal explants were grown in RPMI-1640, 10% fetal bovine serum (HyClone), 2% chick serum (Invitrogen, Carlsbad, Calif.), 100 U/ml penicillin, 0.1 mg/ml streptomycin and 0.025 μg/ml amphotericin (Sigma). N-cadherin peptidomimetic small molecules, reconstituted in either DMSO or 0.3% cyclodextrin at an appropriate working concentration, were further diluted in the culture medium and added at the time of plating. Controls consisted of explants cultured on the same substrate with either DMSO or cyclodextrin diluted in culture medium. Adjacent explants from one retina were alternated between experimental and control dishes to allow for comparison of neurite outgrowth from retinal ganglion cells (RGCs) in adjacent retinal regions. Neurite outgrowth was evaluated approximately 20 hours after plating. Retinal explants were fixed with 4% paraformaldehyde (PFA), 0.01% glutaraldehyde in PEM buffer (80 mM Pipes, 5 mM EGTA, 1 mM $MgCl_2$, 3% sucrose) pH 7.4 for 30 minutes at room temperature prior to imaging. If outgrowth was affected, subsequent experiments determined the minimum concentration to affect outgrowth. A minimum of two independent experiments was conducted per compound with a minimum of 12 explants per condition.

Quantification of Neurite Outgrowth

Neurite outgrowth was examined on a Nikon TE-200 inverted microscope (Tokyo, Japan), using a 10× objective. Images of neurite outgrowth from the retinal explants were collected using a SPOT-RT digital camera and image acquisition software (Diagnostic Instruments, Inc.; Sterling Heights, Mich.). One image per explant was collected from a similar region on the experimental and control dishes. Subsequently measurements of neurite length and density were quantitated using the images. Length of the five longest neurites per explant was measured using MetaMorph version 6.3r4 (Molecular Devices, Downington Pa.). In order to measure density in captured images, neurites were thresholded, binarized and skeletonized to one-pixel width in MetaMorph. This method accounted for variations in neurite fasciculation and yielded consistent numbers of pixels per region to calculate density. Length and density measurements from each experimental explant were normalized to the measurements acquired from the adjacent control explant to yield a percent of control value. Control and experimental conditions were analyzed using the same thresholding parameters. Measurements of a minimum of 12 retinal explants were included for each small molecule tested. The data were combined to yield averages and standard errors in Microsoft Excel.

Adhesion Assay

Sterile 35 mm tissue culture dishes were coated with nitrocellulose in methanol and allowed to dry. Distinct spots, containing 50 ng of either purified Laminin (Sigma) or N-cadherin-Fc (R&D Systems), were made by spotting 10 μl of protein solution on the nitrocellulose-coated tissue culture dishes. Each dish contained two distinct spots of both Laminin and N-cadherin-Fc. After a 20-min incubation at room temperature, the protein solutions were aspirated. Remaining binding sites on the nitrocellulose were blocked with 2% BSA in PBS, and the dishes were rinsed with DMEM (Invitrogen).

LN-229 (American Type Culture Collection, Manassus, Va.) cells plated the previous day in 100 mm tissue culture dishes and grown to 80% confluence were released with 2 mM EDTA in CMF. $4 \times 10^5$ cells were added to each tissue culture dish in the presence of N-cadherin peptidomimetic small molecules, reconstituted in either DMSO or 0.3% cyclodextrin, and diluted in DMEM supplemented with 10% fetal bovine serum (HyClone). In the control experiments, either DMSO or cyclodextrin was added with LN-229 cells in the absence of the peptidomimetic small molecules. The cells were allowed to adhere to the protein substrate for 2 hours at 37° C., 5% $CO_2$. After incubation, the medium was removed and the tissue culture dishes were rinsed once with PBS to remove any unattached cells. Cells were fixed with 4% PFA, 0.01% glutaraldehyde in PEM buffer for 10 minutes at room temperature and rinsed once in PBS prior to imaging.

Quantitation of Adherent Cells

Adherent cells were detected by phase contrast light microscopy using a 20× objective on a Nikon TE-200 inverted microscope. For each experiment, three images per protein substrate spot were acquired with a SPOT-RT digital camera and image acquisition software, resulting in six images for Laminin and six images for N-cadherin per each plating condition tested. The number of adherent cells per image was determined using threshold parameters in Meta-Morph that highlighted individual cells that spread on the substrate spots. The number of highlighted cells from the six images per substrate was combined to yield a total number of adherent cells on that substrate per dish. Data from control and experimental conditions were evaluated using the same thresholding parameters. The number of adherent cells per protein spot in the test dishes was normalized to the number of adherent cells in control dishes to yield a percent of control value. For each small molecule tested, four replicates were combined from two separate experiments to yield averages and standard errors in Microsoft Excel.

ADH-1 Reduces N-Cadherin-Mediated RGC Neurite Outgrowth

Figure 16:
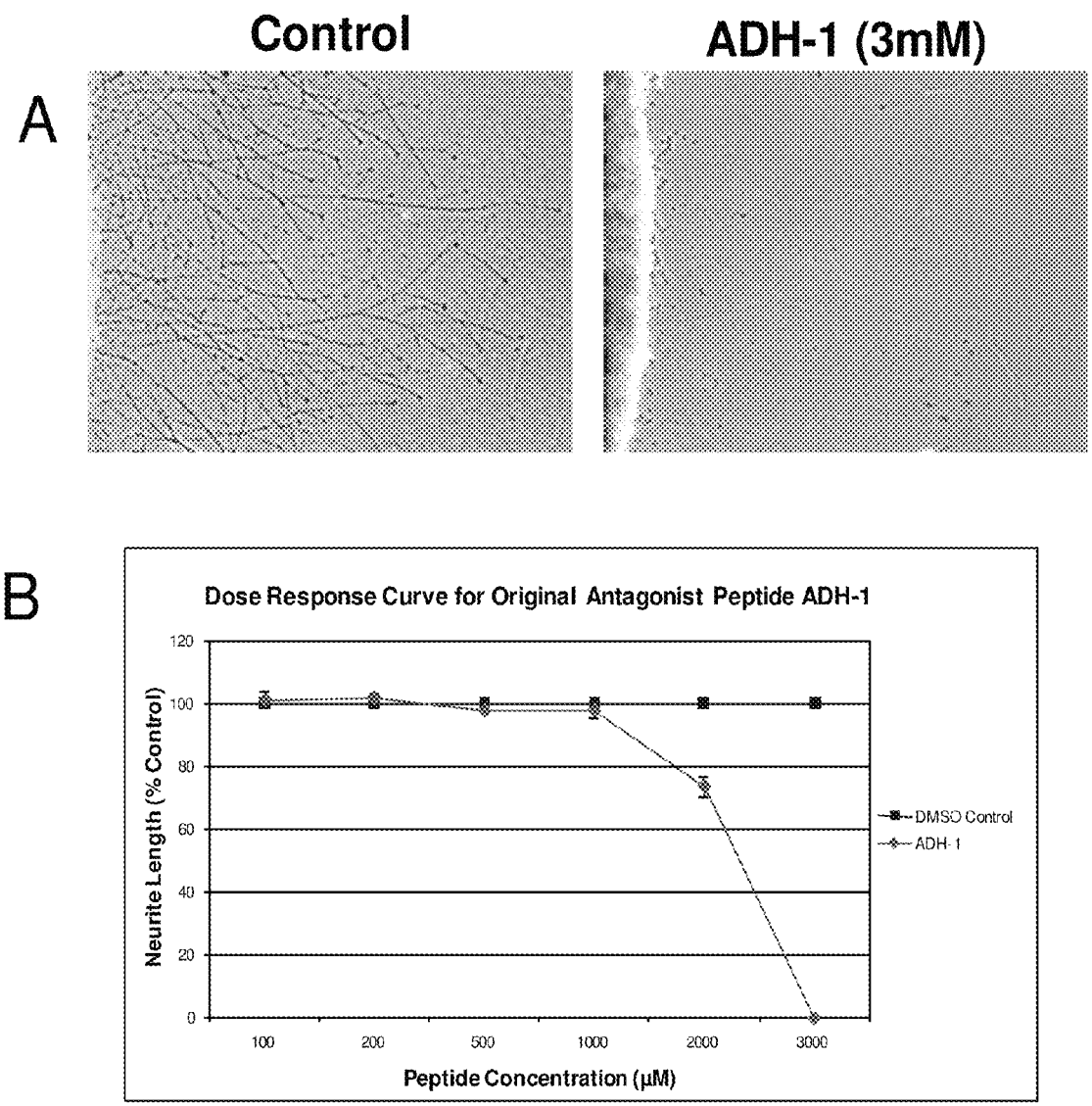
FIGS. 16A-B illustrate images (A) showing peptide antagonist ADH-1 reduces RGC neurite length and density on a N-cadherin substrate compared to vehicle control and (B) dose response analysis of ADH-1 for reduction of neurite length on N-cadherin. Error bars represent standard error calculations.

Analysis of the amino acid sequence of N-cadherin from mouse, rat, human and chick demonstrates a highly conserved histidine alanine valine sequence at amino acids 79- of the membrane distal EC1 domain. A short cyclic HAV peptide N-Ac-CHAVC-$NH_2$ (SEQ ID NO: 3), termed ADH-1, comprising the HAV cadherin cell adhesion recognition sequence, was designed to perturb N-cadherin function. ADH-1 has the ability to inhibit cerebellar neuron neurite outgrowth on an N-cadherin substrate. We determined that ADH-1 is also able to eliminate RGC neurite outgrowth on a substrate of N-cadherin (FIG. 16A). A dose response curve demonstrates that the IC50 of ADH-1 for inhibition of RGC neurite outgrowth is 2.33 mM (FIG. 16B).

Figure 17:
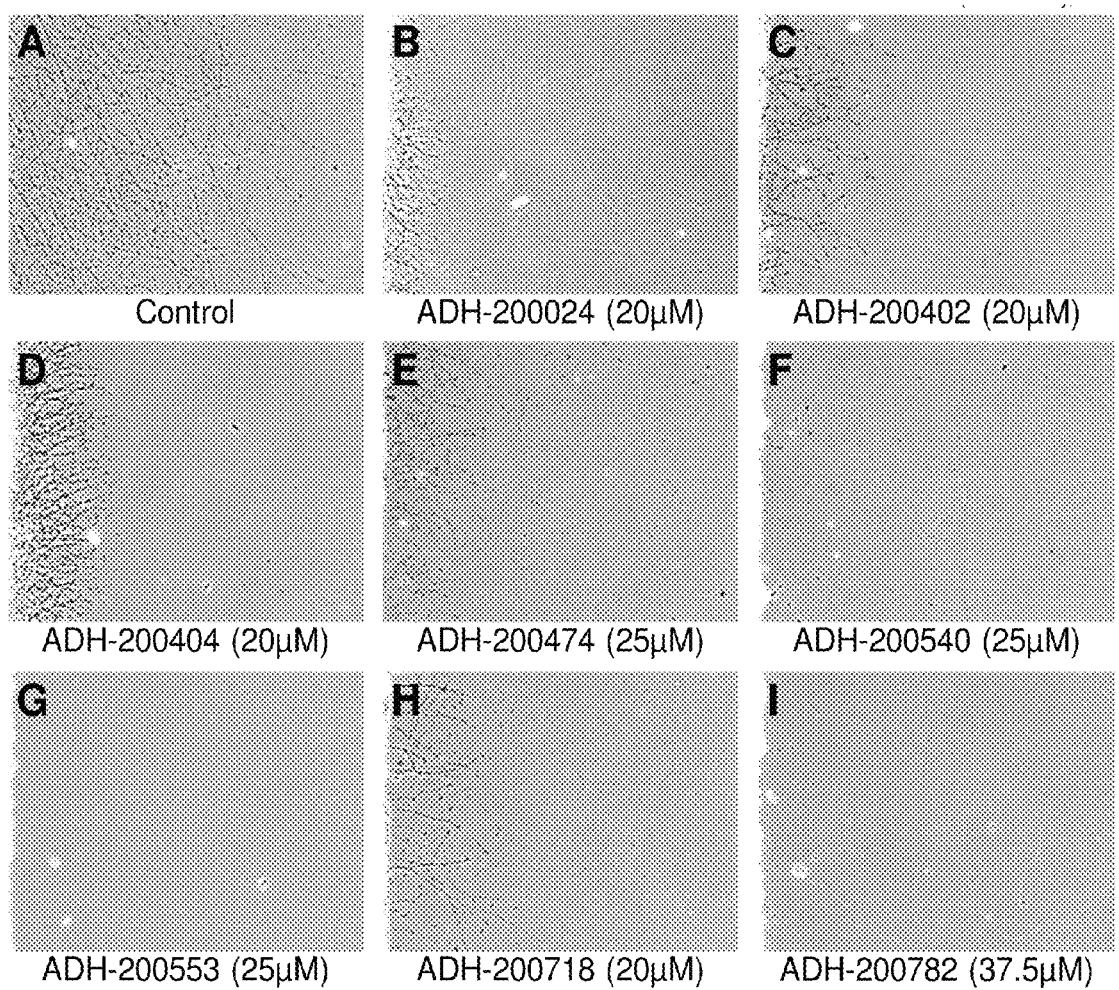
FIGS. 17A-I are a series of photographs illustrating small molecule mimetics of N-cadherin HAV are potent antagonists of N-cadherin-mediated RGC neurite outgrowth. Compared to vehicle control treated RGC outgrowth (A), addition of 20-37.5 μM of these small molecules reduced both neurite length and density on an N-cadherin substrate (B-I).

Small Molecule Peptidomimetics Designed to Mimic the HAV Region of N-Cadherin Inhibit RGC Neurite Outgrowth on N-Cadherin We evaluated peptidomimetic small molecules identified with three-dimensional similarities to ADH-1 in RGC neurite outgrowth assays on an N-cadherin substrate and compared them to vehicle control treated cultures. From these experiments, eight compounds yielded substantial reduction of neurite length and density compared to control at relatively low concentrations between 20-37.5 μM (FIG. 17). The average neurite length in the presence of these compounds was 3.4%-32.4% and density was 0.5%-34.7%, compared to vehicle control neurite outgrowth on N-cadherin (FIG. 18A, B). Dose-response experiments demonstrate that the IC$_{50}$ for all of the compounds is between 4.5 μM (for ADH200553) and 30 μM (for ADH200782) (FIG. 19). These peptidomimetic small molecules were the most potent antagonists of RGC neurite outgrowth identified in our study and are thus designated as strong antagonists.

Figure 18:
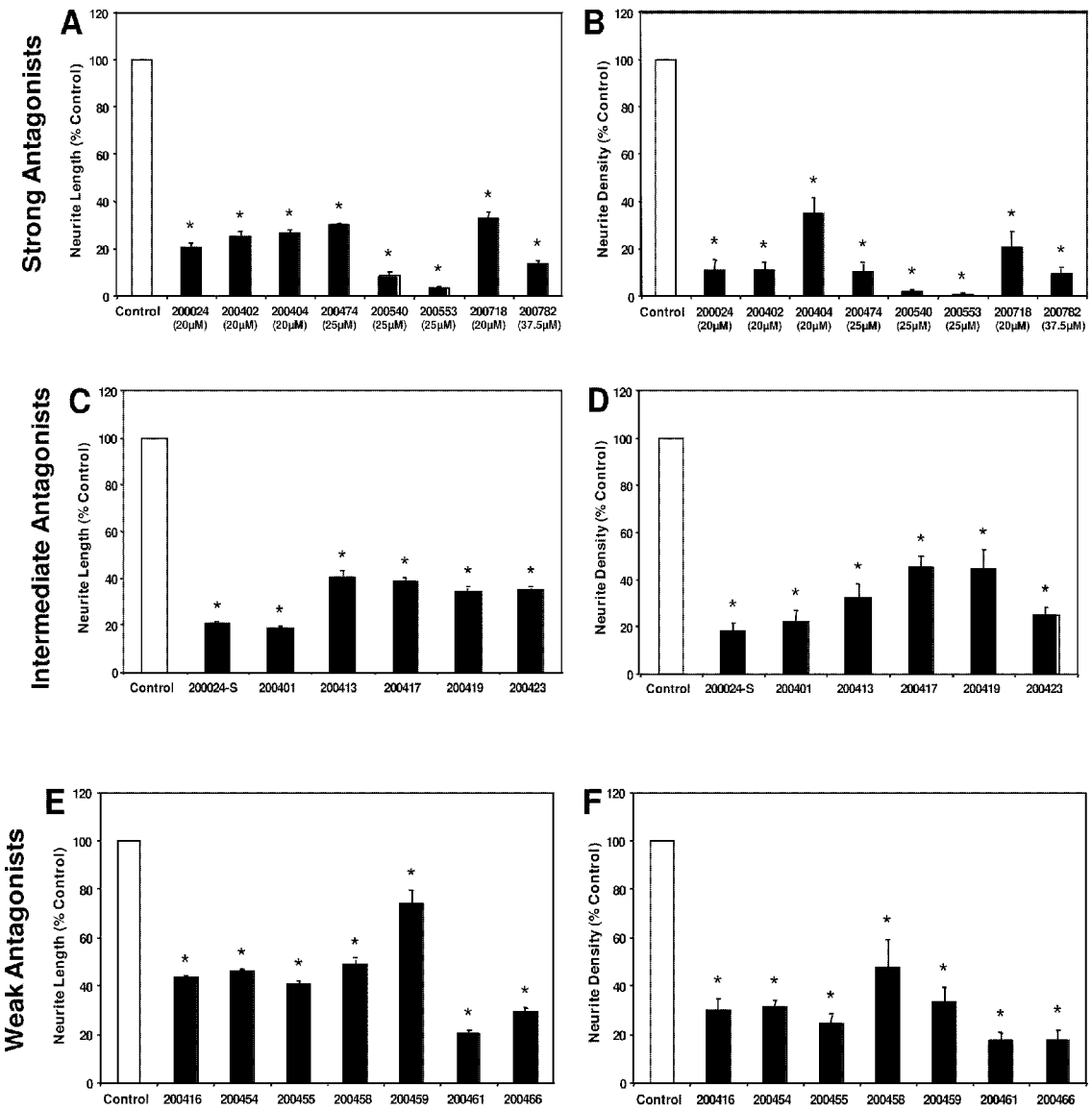
FIGS. 18A-F are a series of charts illustrating average neurite length (A, C, E) and density (B, D, F) on N-cadherin in the presence of the strong (A-B), intermediate (C-D) and weak (E-F) small molecule antagonists. Concentration of strong molecules is indicated. Intermediate and weak molecules were tested at 50 μM and 100 μM, respectively. Error bars represent standard error calculations. Asterisks represent statistical significance from control using the student's t-test ($p<0.001$).

Thirteen additional peptidomimetic small molecules reduced both neurite length and density compared to control at concentrations of 50 μM-100 μM (FIG. 18). These antagonists were classified into two categories, intermediate (FIG. 18 C, D) and weak (FIG. 18 E, F), based on the minimum concentration necessary to produce maximum inhibition. The intermediate antagonists reduced neurite length to 18.5%-40.5% of control and density to 18.1%-45.1% of control at 50 μM. Weak antagonists reduced neurite length to 20.5%-74.2% of control and density to 17.5%-47.8% of control at concentrations of 100 μM.

Figure 20:
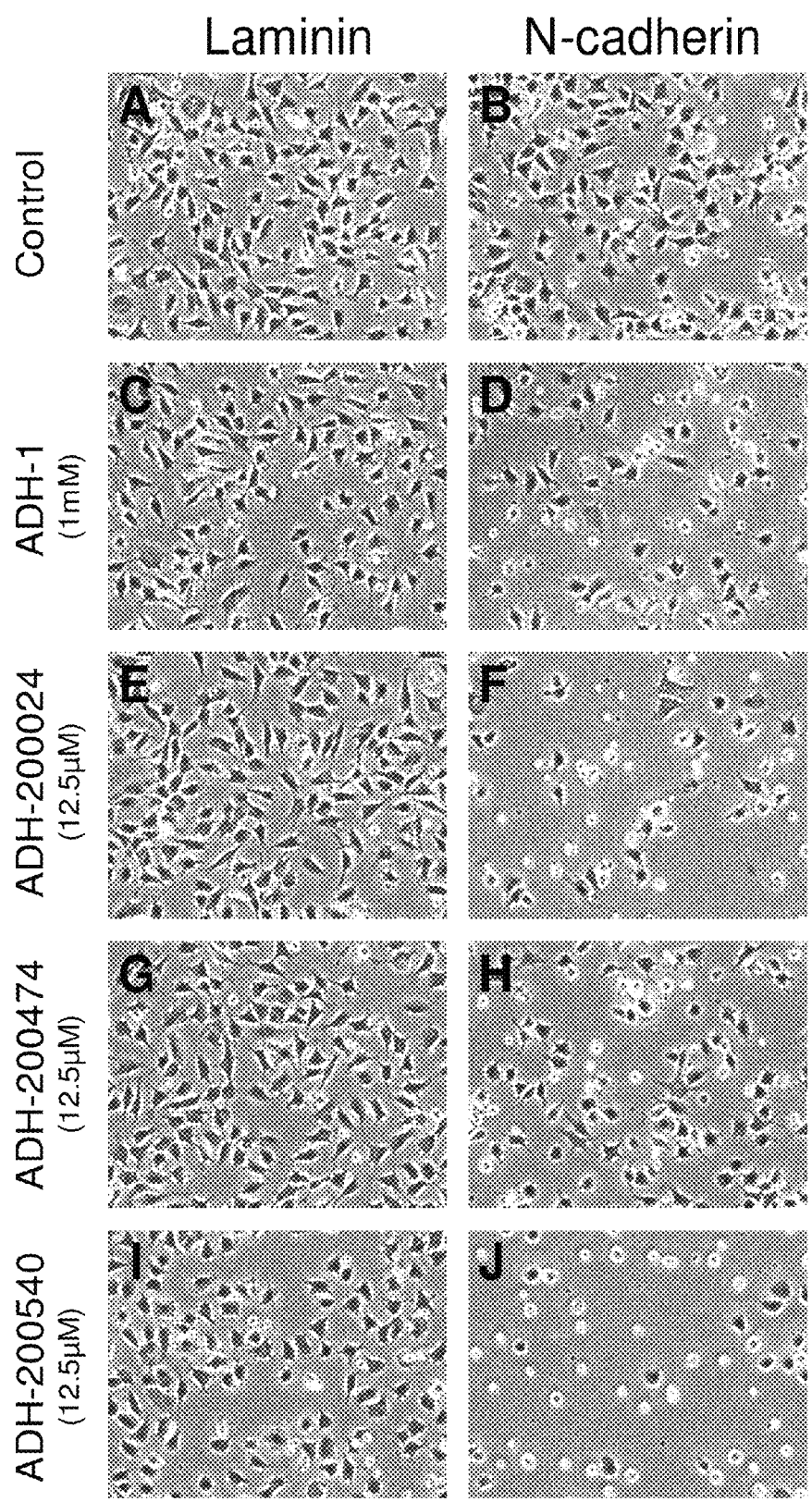
FIGS. 20A-I are a series of images illustrating glioblastoma adhesion to N-cadherin is inhibited in the presence of the strong small molecule antagonists. Addition of 1 mM ADH-1 (C, D) or 12.5 μM of the strong small molecule antagonists (E-J) reduced LN-229 adhesion to N-cadherin (D, F, H, J) compared to vehicle control adhesion (B). Adhesion to Laminin (C, E, G, I) was unaffected by ADH-1 (C) or the small molecule antagonists (E, G, I) compared to control (A).
Figure 21:
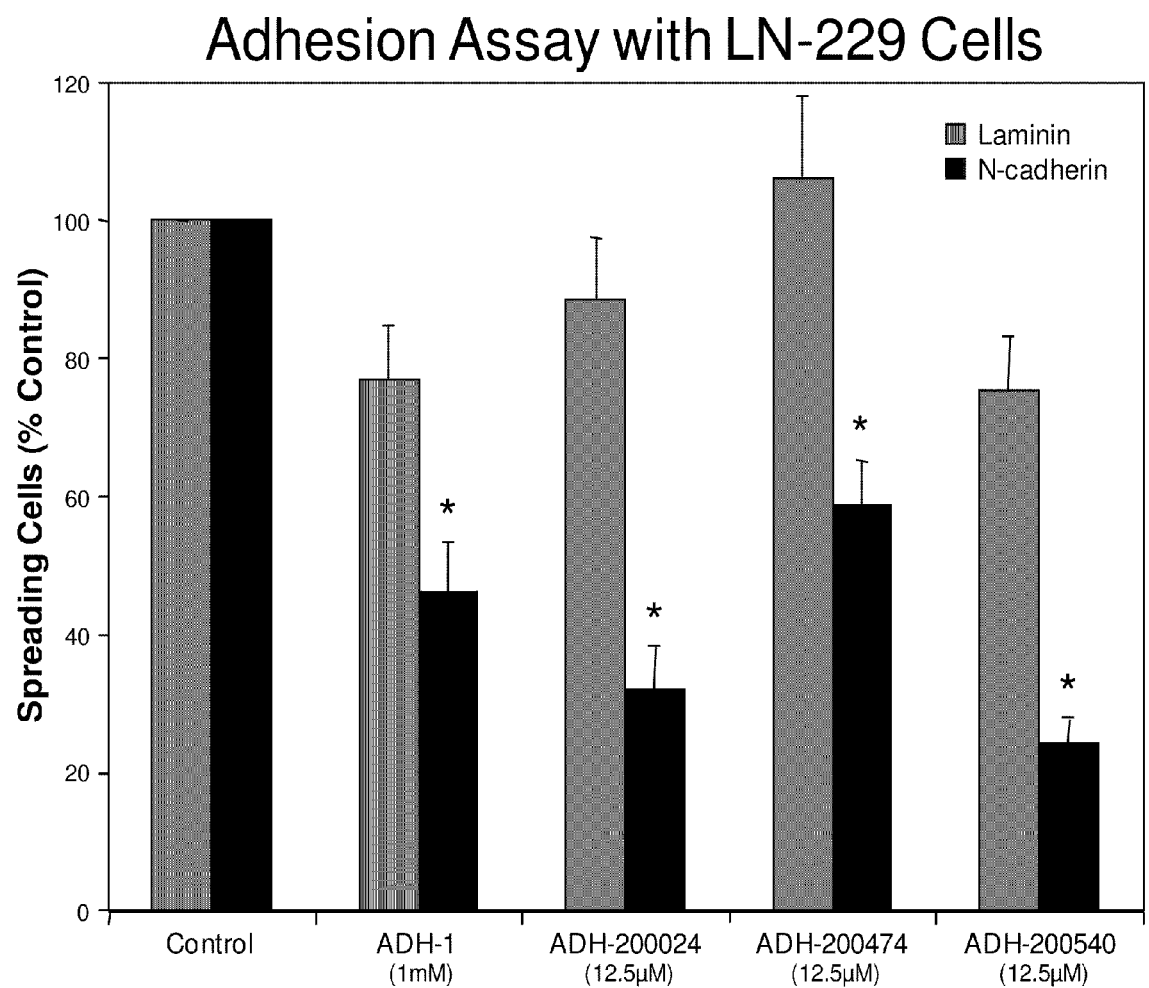
FIG. 21 is a chart illustrating average Glioblastoma cell adhesion to N-cadherin in the presence of strong small molecule antagonists or ADH-1. Addition of ADH-1 or the strong small molecule antagonists reduced LN-229 adhesion to N-cadherin compared to vehicle control adhesion. Adhesion to Laminin was unaffected by ADH-1 or the small molecule antagonists compared to control. Error bars represent standard error. Asterisks represent statistical significance using student's t-test (p<0.001).

Effects of Peptidomimetic Small Molecules on N-Cadherin-Mediated LN-229 Adhesion Human glioblastoma LN-229 cells express N-cadherin and adhere to a purified N-cadherin substrate (FIG. 20). We observed that ADH-1 reduced adhesion of LN-229 cells to an N-cadherin substrate to 46% of control at a dose of 1 mM (FIGS. 20-21). We tested the ability of the strong antagonist peptidomimetic small molecules identified in neurite outgrowth experiments to perturb N-cadherin-mediated adhesion of LN-229 glioblastoma cells. The tested antagonists blocked N-cadherin-mediated adhesion of LN-229 cells to an N-cadherin substrate, but did not affect LN-229 cell adhesion to Laminin (FIGS. 20-21). Average adhesion to N-cadherin following addition of the strong small molecule antagonists was between 24.3%-58.9% of control (FIG. 21).

EXAMPLE 3

Cadherin Agonists Stimulate N-Cadherin-Dependent Neurite Outgrowth

Figure 22:
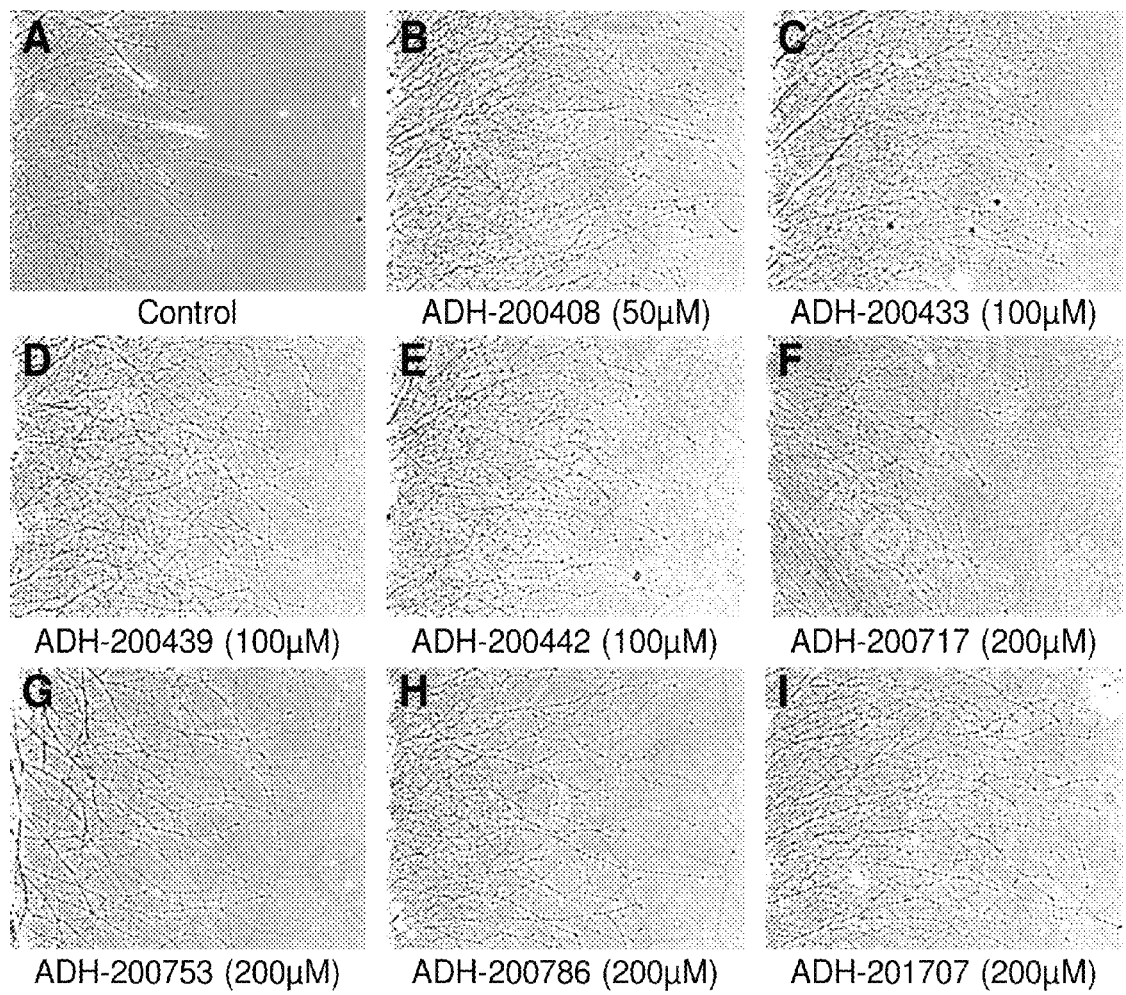
FIG. 22 is a series of photographs showing that agonists stimulate N-cadherin-mediated RGC neurite outgrowth.
Figure 23:
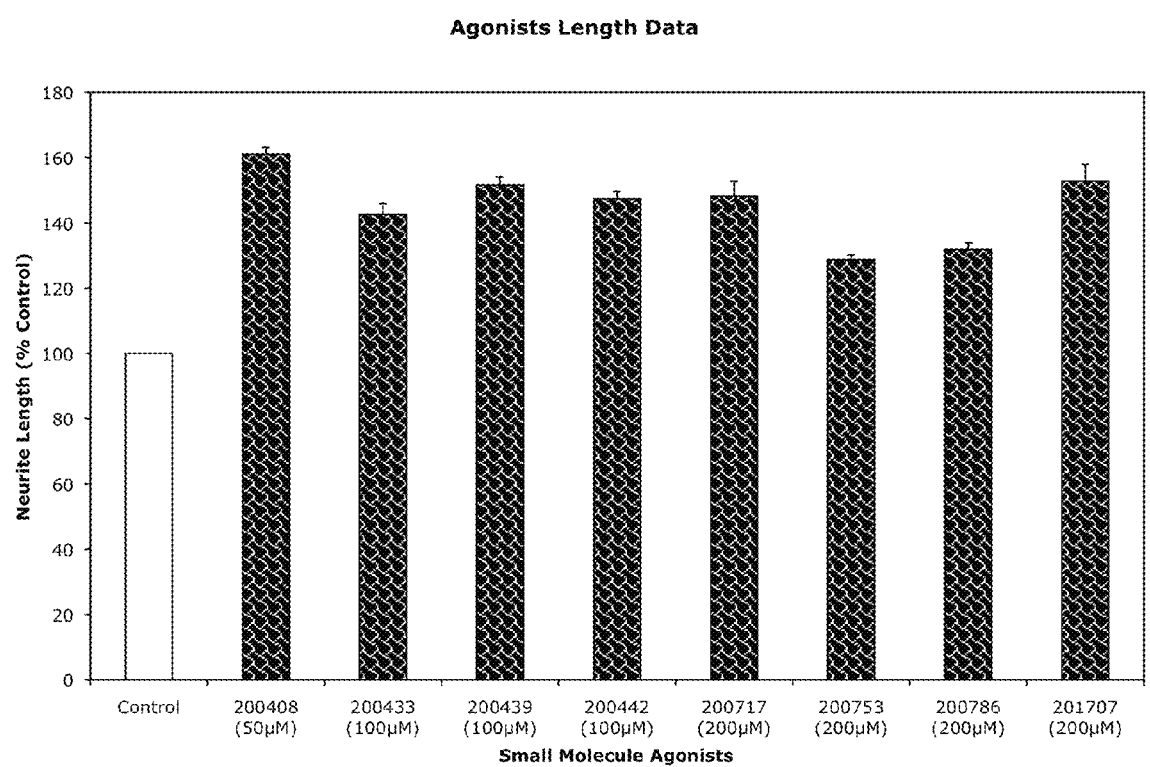
FIG. 23 is a chart showing length of RGC neurite outgrowth stimulated by small molecule peptidomimetic agonists.
Figure 24:
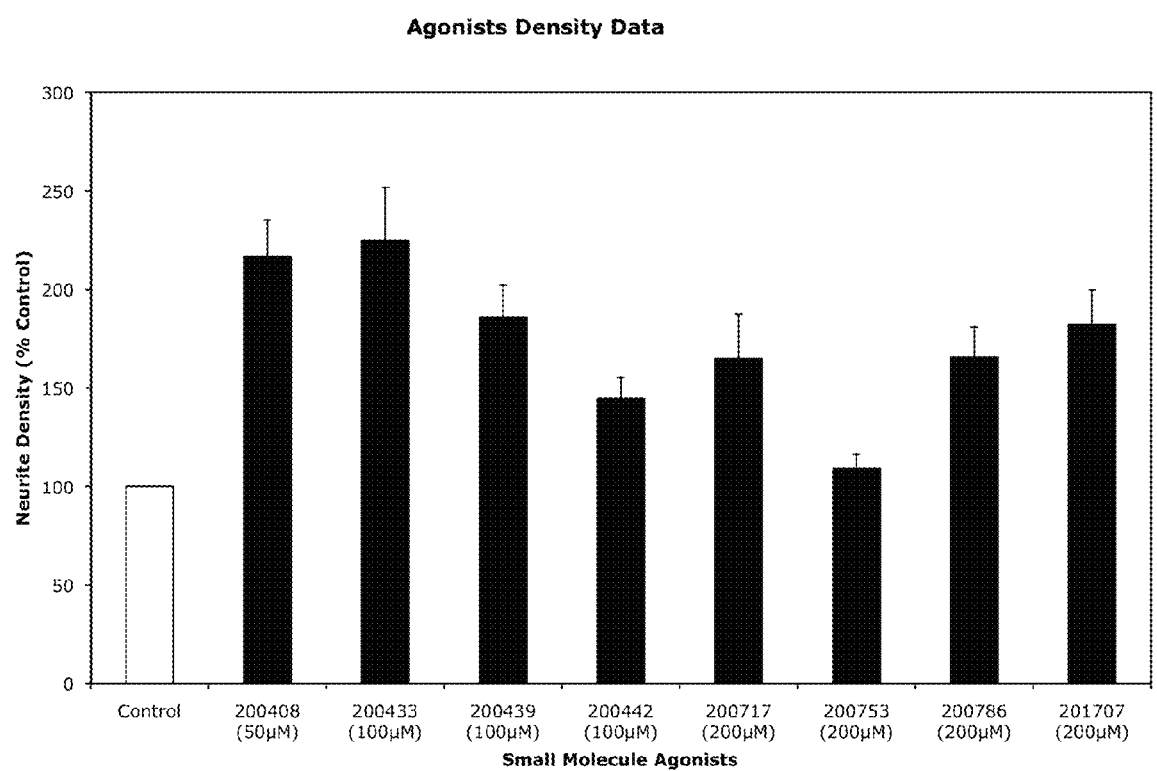
FIG. 24 is a chart showing neurite density of RGC neurite outgrowth stimulated by small molecule peptidomimetic agonists.
Figure 25:
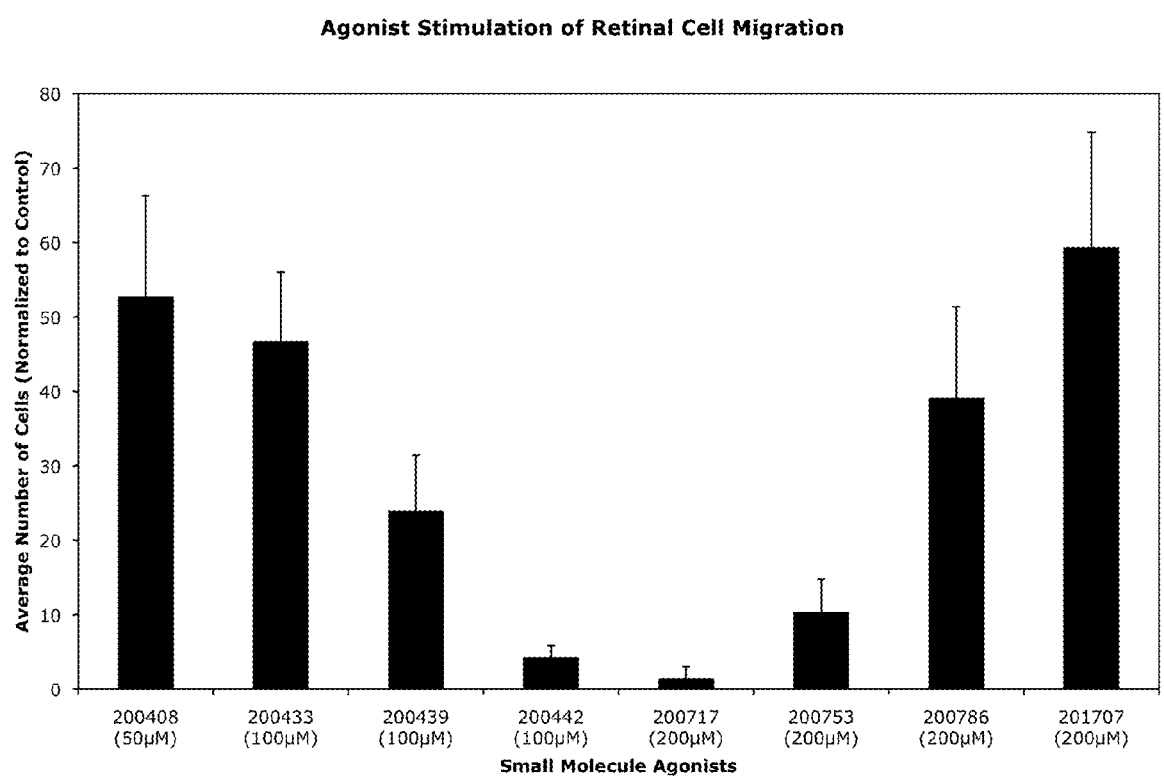
FIG. 25 is a chart showing retinal cell migration stimulated by small molecule peptidomimetic agonists.

E8 chick retinal explants were cultured on an N-cadherin substrate for 24 hours in the presence of either control or an agonist to N-cadherin similar to the method in Example 2. N-cadherin-dependent neurite outgrowth was tested at a lower concentration of N-cadherin substrate to distinguish stimulation of neurite outgrowth. From these experiments as shown in the following Table, eight compounds yielded substantial increase (e.g., about 150% to about 200%) of neurite outgrowth for both length and density compared to control at concentrations of 50 μM to 200 μM (FIG. 22-24). FIG. 25 also illustrates that the eight agonists also stimulated retinal cell migration from about 3% to about 60% of control when administered at about 50 μM to about 200 μM.

TABLE

Agonist Data

| | Concentration | | | | | | |
|---|---|---|---|---|---|---|---|
| | 50 μM | | 100 μM | | 200 μM | | |
| Compound | Length | Density | Length | Density | Length | Density | Number |
| ADH200408 | 161.1 | 216.7 | | | | | 20 |
| StdErr | 2.1 | 18.6 | | | | | |
| ADH200433 | | | 142.5 | 224.8 | | | 18 |
| StdErr | | | 3.5 | 26.9 | | | |
| ADH200439 | | | 151.6 | 185.7 | | | 18 |
| StdErr | | | 2.5 | 16.4 | | | |
| ADH200442 | | | 147.4 | 144.7 | | | 18 |
| StdErr | | | 2.3 | 10.7 | | | |
| ADH200717 | | | | | 148.2 | 164.8 | 12 |
| StdErr | | | | | 4.6 | 22.7 | |
| ADH200753 | | | | | 128.7 | 109.2 | 18 |
| StdErr | | | | | 1.4 | 7.0 | |
| ADH200786 | | | | | 131.9 | 165.9 | 18 |
| StdErr | | | | | 2.0 | 15.4 | |
| ADH201707 | | | | | 152.8 | 182.1 | 18 |
| StdErr | | | | | 5.1 | 17.7 | |

From the above description of the invention, those skilled in the art will perceive improvements, changes and modifications. Such improvements, changes, and modifications are within the skill of the art and are intended to be covered by the appended claims.

Having described the invention, the following is claimed:

1. A method for promoting neurite outgrowth and neuronal migration, the method comprising the steps of:
   selecting a cadherin agonist that promotes neurite outgrowth when applied to at least one neuron disposed on a substrate coated with a purified cadherin molecule, wherein the cadherin agonist is determined to be a cadherin agonist by applying a potential cadherin modulating agent to the at least one neuron disposed on the substrate coated with the cadherin molecule and evaluating neurite outgrowth on the substrate; wherein an increase in neurite outgrowth of the at least one neuron as compared to a control indicates that the potential cadherin modulating agent is a cadherin agonist capable of promoting neurite outgrowth; and
   contacting at least one neuron with the cadherin agonist in an amount effective to promote neurite outgrowth, the cadherin agonist including a small molecule peptidomimetic of a peptide or cyclic peptide that comprises a cadherin cell adhesion recognition sequence.

2. The method of claim 1, wherein the selected cadherin agonist increases neurite outgrowth at least about 101% of the at least one neuron disposed on a substrate coated with a cadherin molecule as compared to a control.

3. The method of claim 2, wherein the selected cadherin agonist increases neurite outgrowth at least about 120% of the at least one neuron disposed on the substrate coated with the cadherin molecule as compared to a control.

4. The method of claim 1, wherein the potential cadherin modulating agent includes a small molecule peptidomimetic of a peptide or cyclic peptide that comprises a cadherin cell adhesion recognition sequence.

5. The method of claim 1, the step of applying a potential cadherin modulating agent to the at least one neuron further comprising the steps of:
   coating a surface of a culture vessel to form the substrate;
   coating a portion of the substrate with a cadherin molecule;
   preparing a tissue explant comprising the at least one neuron; and
   placing the tissue explant in contact with a portion of the substrate that includes the cadherin molecule.

6. The method of claim 5, the step of preparing a tissue explant further comprising the steps of:
   coating a filter having a major surface with a substance capable of promoting cell adherence; and
   placing the tissue explant onto the major surface of the filter such that the at least one neuron is in contact with the major surface.

7. The method of claim 6, the substance capable of promoting cell adherence comprising a lectin.

8. The method of claim 4 the step of evaluating neurite outgrowth on the substrate further comprising the steps of:
   measuring neurite outgrowth from the tissue explant; and
   determining neurite length, density, or a combination thereof.

9. The method of claim 1, the cadherin cell adhesion recognition sequence comprising SEQ ID NO: 1 or SEQ ID NO: 2.

* * * * *